(12) United States Patent
Sasikumar et al.

(10) Patent No.: US 9,044,442 B2
(45) Date of Patent: Jun. 2, 2015

(54) PEPTIDOMIMETIC COMPOUNDS AS IMMUNOMODULATORS

(71) Applicant: AURIGENE DISCOVERY TECHNOLOGIES LIMITED, Bangalore (IN)

(72) Inventors: Pottayil Govindan Nair Sasikumar, Bangalore (IN); Muralidhara Ramachandra, Bangalore (IN); Seetharamaiah Setty Sudarshan Naremaddepalli, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

(21) Appl. No.: 13/787,877

(22) Filed: Mar. 7, 2013

(65) Prior Publication Data

US 2013/0237580 A1     Sep. 12, 2013

(30) Foreign Application Priority Data

Mar. 7, 2012   (IN) .............................. 854/CHE/2012

(51) Int. Cl.

| | | |
|---|---|---|
| C07C 243/34 | (2006.01) | |
| C07C 275/16 | (2006.01) | |
| C07C 335/08 | (2006.01) | |
| C07C 327/56 | (2006.01) | |
| C07D 209/20 | (2006.01) | |
| A61K 31/17 | (2006.01) | |
| A61K 31/405 | (2006.01) | |
| A61P 35/00 | (2006.01) | |
| A61K 31/197 | (2006.01) | |
| A61K 31/16 | (2006.01) | |
| A61K 31/222 | (2006.01) | |
| C07D 209/18 | (2006.01) | |
| A61K 45/06 | (2006.01) | |
| C07K 5/02 | (2006.01) | |

(52) U.S. Cl.
CPC .............. *A61K 31/197* (2013.01); *C07C 243/34* (2013.01); *A61K 31/16* (2013.01); *C07C 275/16* (2013.01); *A61K 31/222* (2013.01); *C07D 209/18* (2013.01); *A61K 31/405* (2013.01); *C07C 335/08* (2013.01); *A61K 45/06* (2013.01); *C07K 5/0217* (2013.01); *C07C 327/56* (2013.01); *C07D 209/20* (2013.01)

(58) Field of Classification Search
CPC .. C07C 243/34; C07C 275/16; C07C 335/08; C07C 327/56; C07D 209/20; A61K 31/17; A61K 31/405

USPC .......... 514/614, 588, 563, 565; 564/464, 123, 564/148, 32
See application file for complete search history.

(56) References Cited

U.S. PATENT DOCUMENTS

| | | |
|---|---|---|
| 2007/0065427 A1 | 3/2007 | Freeman et al. |
| 2008/0311117 A1 | 12/2008 | Collins et al. |
| 2011/0033884 A1 | 2/2011 | Wood et al. |
| 2011/0081341 A1 | 4/2011 | Honjo et al. |
| 2011/0318373 A1 | 12/2011 | Sasikumar et al. |
| 2012/0027759 A1 | 2/2012 | Chen et al. |
| 2013/0022629 A1 | 1/2013 | Sharpe et al. |

FOREIGN PATENT DOCUMENTS

| | | | | |
|---|---|---|---|---|
| WO | 01/14557 | | 3/2001 | |
| WO | WO 02/066512 | * | 8/2002 | ............. C07K 14/78 |

OTHER PUBLICATIONS

Vagner et al. Current Oppinion in Chemical Biology 2008, 12, 292-296.*
Yasutoshi Agata et al.: Expression of the PD-1 antigen on the surface of stimulated mouse T and B lymphocytes; International Immunology, vol. 8, No. 5, pp. 765-772.
Joseph Illingworth et al: Chronic Exposure to Plasmodium falciparum Is Associated with Phenotypic Evidence of B and T Cell Exhaustion; The Journal of Immunology; J Immunol 2013, 190, pp. 1038-1047.
Prokunina et al: A regulatory polymorphism in PDCD1 is associated with susceptibility to systemic lupus erythematosus in humans; Nature Genetics, vol. 32, Dec. 2002; pp. 666-669.
Suzanne L. Topalian et al.: Safety, Activity, and Immune Correlates of Anti-PD-1 Antibody in Cancer; Jun. 28, 2012 vol. 366 No. 26; The New England Journal of Medicine; pp. 2443-2454.
Julie R. Brahmer et al.: Safety and Activity of Anti-PD-L1 Antibody in Patients with Advanced Cancer; Jun. 28, 2012; The New England Journal of Medicine; pp. 2455-2465.

\* cited by examiner

*Primary Examiner* — Sreeni Padmanabhan
*Assistant Examiner* — Irina Neagu
(74) *Attorney, Agent, or Firm* — Benjamin Aaron Adler

(57) ABSTRACT

The present invention relates to novel peptidomimetic compounds as therapeutic agents capable of inhibiting the programmed cell death 1 (PD1) signalling pathway. The invention also relates to derivatives of the therapeutic agents. The invention also encompasses the use of the said therapeutic agents and derivatives for treatment of disorders via immunopotentiation comprising inhibition of immunosuppressive signal induced due to PD-1, PD-L1, or PD-L2 and therapies using them.

11 Claims, 3 Drawing Sheets

Figure 1: Dose response effect of compounds 2, 12 & 13 in mouse splenocyte proliferation assay using recombinant hPDL1
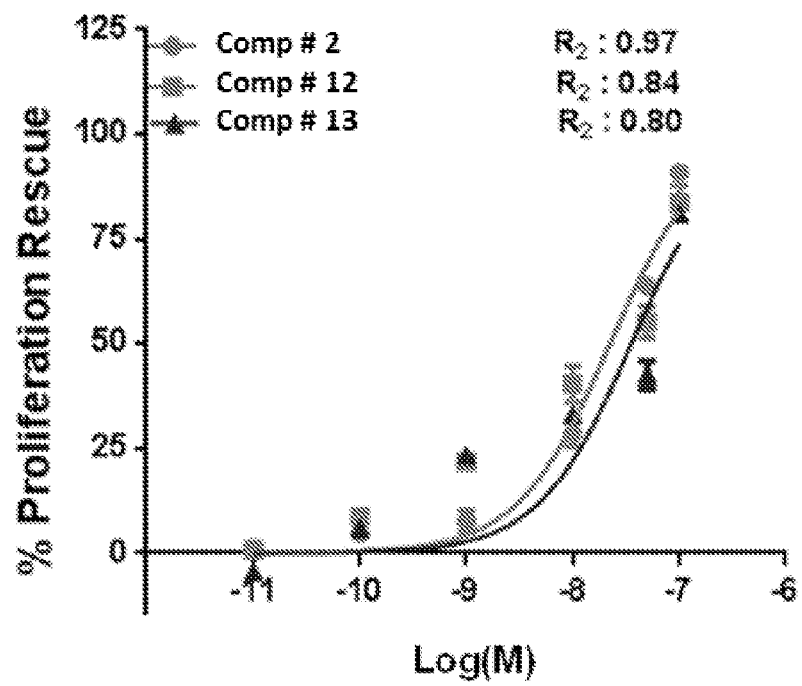

Figure 2: In vivo efficacy of compound #2 on primary tumour growth in CT-26 colon cancer model
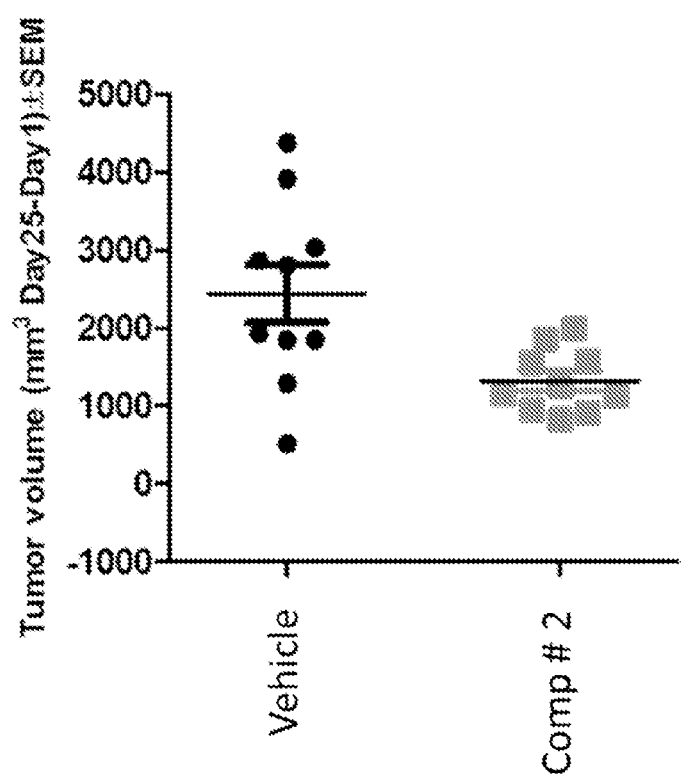

Figure 3: In vivo efficacy of compound 2 against Pseudomonas aeruginosa lung infection model
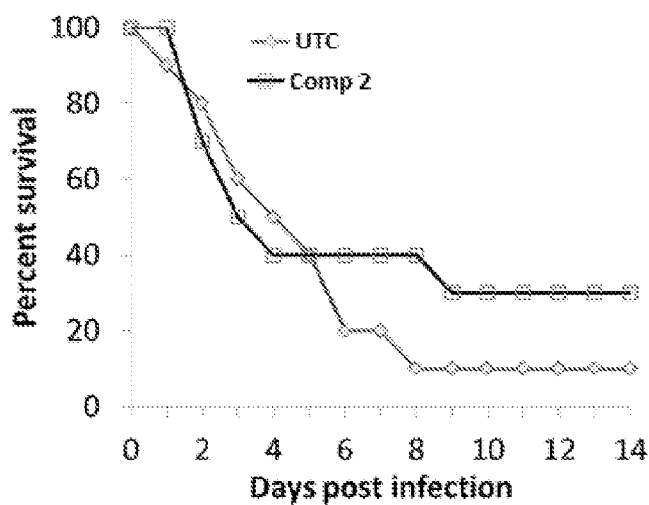

PEPTIDOMIMETIC COMPOUNDS AS IMMUNOMODULATORS

This application claims the benefit of Indian provisional application number 854/CHE/2012, filed on Mar. 7, 2012; which hereby incorporated by reference.

FIELD OF TECHNOLOGY

The present invention relates to novel peptidomimetic compounds therapeutically useful as immune modulators. The invention also relates to pharmaceutical compositions comprising the said novel peptidomimetic compounds and their derivatives as therapeutic agents.

BACKGROUND

Immune system in mammals possesses the ability to control the homeostasis between the activation and inactivation of lymphocytes through various regulatory mechanisms during and after an immune response. Among these mechanisms, there are mechanisms that specifically modulate the immune response as and when required. Mechanism via PD-1 pathway relates to almost every aspect of immune responses including autoimmunity, tumour immunity, infectious immunity, transplantation immunity, allergy and immunological privilege. PD-1 (or Programmed Cell Death 1 or PDCD1) is a ~55 kD type I membrane glycoprotein and is a receptor of the CD28 superfamily that negatively regulates T cell antigen receptor signalling by interacting with the specific ligands and is suggested to play significant role in the maintenance of self-tolerance.

The PD-1 protein's structure comprises of an extracellular IgV domain followed by a trans-membrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals. Also, PD-1 is expressed on the surface of activated T cells, B cells, and macrophages, (Y. Agata et al., Int Immunol, May 1996, 8, 765) suggesting that compared to CTLA-4 [(Cytotoxic T-Lymphocyte Antigen 4), also known as CD152 (Cluster of differentiation 152), a protein that also plays an important regulatory role in the immune system], PD-1 more broadly negatively regulates immune responses.

Indeed, functional "exhaustion" (immune dysfunction) among T and B cell subsets is a well-described feature of chronic viral infections, such as hepatitis B and C and HIV viruses. T cell exhaustion was initially described for CD8 T cells in mice chronically infected with lymphocytic choriomeningitis virus clone 13. In the lymphocytic choriomeningitis virus mouse model, repeated antigen stimulation through the T cell antigen receptor drives the sustained expression of T cell inhibitory receptors, including programmed cell death-1 (PD-1) and lymphocyte activation-gene-3 (LAG-3), on virus-specific CD8 T cells (Joseph Illingworth et al., Journal of Immunology (2013), 190(3), 1038-1047).

Blockade of PD-1, an inhibitory receptor expressed by T cells, can overcome immune resistance. (PD-1 is a key immune check point receptor expressed by activated T cells, and it mediates immune suppression. PD-1 functions primarily in peripheral tissues, where T cells may encounter the immune suppressive PD-1 ligands; PD-L1 (B7-H1) and PD-L2 (B7-DC), which are expressed by tumor cells, stromal cells, or both Inhibition of the interaction between PD-1 and PD-L1 can enhance T-cell responses in vitro and mediate preclinical antitumor activity (Suzanne L. Topalian et al., N Engl J. Med. 2012, 366(26): 2443-2454).

PD-1 plays critical roles in the regulation of the immune response to cancer, allergy, and chronic viral infection (Julie R. Brahmer et al., N Engl J. Med. 2012, 366(26): 2455-2465.)

Tumour cells and virus (including HCV and HIV) infected cells are known to exploit the PD-1 signalling pathway (to create Immunosuppression) in order to escape immune surveillance by host T cells. It has been reported that the PD-1 gene is one of genes responsible for autoimmune diseases like systemic lupus erythematosus (Prokunina et al., Nature Genetics, 2002, Vol. 32, No. 4, 666-669.).

Several potential immunomodulators of PD-1 have been described. For example International application WO 01/14557, WO 2004/004771, WO 2004/056875, WO 02/079499, WO 03/042402 and WO 2002/086083 report PD-1 or PD-L1 inhibitory antibody or fusion protein.

United State patent application US2011318373 reports peptide and their derivatives derived from PD1 ectodomain capable of inhibiting the programmed cell death 1 (PD1) signalling pathway.

International application number WO2011/082400 reports heteroaryl compounds and their derivatives as potential immunomodulators of PD-1. Unfortunately, there are no peptidomimetics compounds available currently as PD-1 immunomodulators.

There is a need for more potent, better and/or selective immune modulators of PD-1 pathway. In the present invention, we explore novel peptidomimetic compounds and their therapeutic usefulness as immunomodulatory agents as a new approach. Peptidomimetics compounds often mimic in the structure to peptide and the biological activity while offering the further advantages of increased oral bioavailability, biostability, bioefficiency, the half-life of the activity through minimizing enzymatic degradation, greater distribution within the target tissues such as tumor for improved therapeutic efficacy, higher stability at ambient temperature leading to better storage properties, lower cost of goods and easier regulatory clearance due to lack of issues related to purity such as contamination by cellular materials. The present invention therefore may provide the solution for this by offering novel synthetic peptidomimetic compounds and its derivatives which acts as immune-modulators of PD1 pathway.

BRIEF DESCRIPTION OF ACCOMPANYING DRAWINGS

FIG. 1: Dose response effect of compounds 2, 12 & 13 in mouse splenocyte proliferation assay using recombinant hPDL1.

FIG. 2: In vivo efficacy of compound #2 on primary tumour growth in CT-26 colon cancer model.

FIG. 3: In vivo efficacy of compound 2 against *Pseudomonas aeruginosa* lung infection model.

SUMMARY

In accordance with the present invention, novel peptidomimetic compounds or a stereoisomer thereof or a pharmaceutically acceptable salt thereof, provided which are capable of suppressing and/or inhibiting the programmed cell death 1 (PD1) signalling pathway.

In one aspect, the present invention provides a peptidomimetic compound of formula (I):

$$\text{(I)}$$

[Structure of Formula (I): R₁, R₁' on carbon; R₃R₂N— attached; Rₐ, Rₐ'; R₄, R₄'; R_b, R_b'; N—H—R₅; (CH₂)ₙ—COR_c]

wherein;

R₁ is hydrogen, —OR₆, —OC(O)R₆, halogen, cyano, or hydroxyalkyl;

R₁' is hydrogen or alkyl;

both R_a and R_a' represent hydrogen; or together represent an oxo (=O) group or a thioxo (=S) group;

both R_b and R_b' represent hydrogen; or together represent an oxo (=O) group or a thioxo (=S) group;

R₂ and R₃ are independently selected from hydrogen, optionally substituted alkyl or optionally substituted acyl;

R₄ and R₄' are independently selected from hydrogen, optionally substituted alkyl or optionally substituted acyl;

R₆ is selected from hydrogen or optionally substituted alkyl;

'n' is an integer selected from 1 or 2;

R_c is selected from hydroxyl or amino;

R₅ is hydrogen or a group selected from —C(=X)—Am₁—R₇ or —Am₁—R₈;

wherein, X is selected from O or S;

Am₁ represents an amino acid residue selected from Ser, Asp, Ala, Ile, Phe, Trp, Glu and Thr; wherein the amino acid residue is optionally substituted with alkyl or acyl group;

R₇ is alpha carboxylic group of Am₁ which may be in free acid, ester or in amide form; wherein the said amide nitrogen is optionally substituted with hydroxyl or amino;

R₈ is alpha amino group of Am₁ which is optionally substituted with —CONH-alkyl;

or a stereoisomer thereof or a pharmaceutically acceptable salt thereof.

In a further aspect of the present invention, it relates to the pharmaceutical composition comprising a compound of Formula (I) or a pharmaceutically acceptable salt or a stereoisomer and processes for preparing thereof.

In yet another aspect of the present invention, it provides use of peptidomimetic compounds of Formula (I) and their salts and stereoisomers thereof, which are capable of suppressing and/or inhibiting the programmed cell death 1 (PD1) signaling pathway.

DETAILED DESCRIPTION

The present invention provides novel peptidomimetic compounds as therapeutic agents useful for treatment of disorders via immunopotentiation comprising inhibition of immunosuppressive signal induced due to PD-1, PD-L1, or PD-L2 and therapies using them.

Each embodiment is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents.

Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In one embodiment, the present invention relates to compounds of Formula (I)

$$\text{(I)}$$

[Structure of Formula (I) repeated]

wherein;

R₁ is hydrogen, —OR₆, —OC(O)R₆, halogen, cyano, or hydroxyalkyl;

R₁' is hydrogen or alkyl;

both R_a and R_a' represent hydrogen; or together represent an oxo (=O) group or a thioxo (=S) group;

both R_b and R_b' represent hydrogen; or together represent an oxo (=O) group or a thioxo (=S) group;

R₂ and R₃ are independently selected from hydrogen, optionally substituted alkyl or optionally substituted acyl;

R₄ and R₄' are independently selected from hydrogen, optionally substituted alkyl or optionally substituted acyl;

R₆ is selected from hydrogen or optionally substituted alkyl;

'n' is an integer selected from 1 or 2;

R_c is selected from hydroxyl or amino;

R₅ is hydrogen or a group selected from —C(=X)—Am₁—R₇ or —Am₁—R₈;

wherein, X is selected from O or S;

Am₁ represents an amino acid residue selected from Ser, Asp, Ala, Ile, Phe, Trp, Glu and Thr; wherein the amino acid residue is optionally substituted with alkyl or acyl group;

R₇ is alpha carboxylic group of Am₁ which may be in free acid, ester or in amide form; wherein the said amide nitrogen is optionally substituted with hydroxyl or amino;

R₈ is alpha amino group of Am₁ which is optionally substituted with —CONH-alkyl;

or a stereoisomer thereof or a pharmaceutically acceptable salt thereof.

In another embodiment, R_a and R_a' together represent thioxo (=S) or oxo (=O) group and the remaining groups are same as defined in formula (I).

In one embodiment, the compounds of the present invention have a Formula (IA):

$$\text{(IA)}$$

[Structure of Formula (IA): R₃R₂N—CH(R₁)—C(=O)—NH—N(R₄)—C(=O)—CH((CH₂)ₙCONH₂)—NH—R₅]

wherein, $R_1$, $R_2$, $R_3$, $R_4$, $R_5$ and 'n' are same as defined in Formula (I).

In another embodiment, the compounds of the present invention have a Formula (IB):

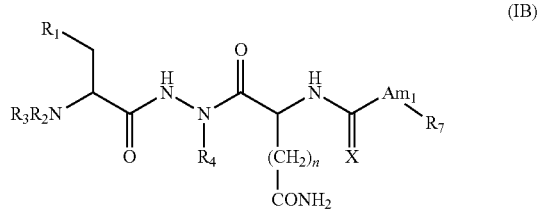

(IB)

wherein, $R_1$, $R_2$, $R_3$, $R_4$, X, $Am_1$, $R_7$ and 'n' are same as defined in Formula (I).

In yet another embodiment, compounds of the present invention have the Formula (IC):

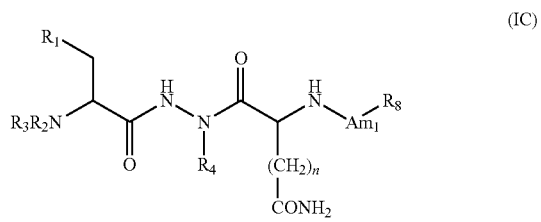

(IC)

wherein, $R_1$, $R_2$, $R_3$, $R_4$, $Am_1$, $R_8$ and 'n' are same as defined in Formula (I).

In yet another embodiment, compounds of the present invention have the Formula (ID):

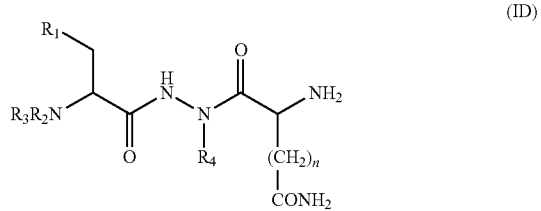

(ID)

wherein, $R_1$, $R_2$, $R_3$, $R_4$ and 'n' are same as defined in Formula (I).

In yet another embodiment, compounds of the present invention have the Formula (IE):

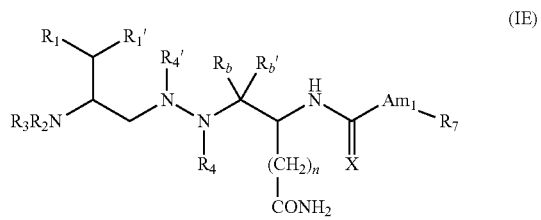

(IE)

wherein, $R_1$, $R_1'$ $R_2$, $R_3$, $R_4$, $R_4'$, $R_b$, $R_b'$, $R_7$, $Am_1$, X and 'n' are same as defined in Formula (I).

In one embodiment, specifically provided are compounds of the Formula (IA), (IB), (IC), (ID) and (IE) in which $R_1$ is —$OR_6$ and $R_6$ is hydrogen.

In another embodiment, specifically provided are compounds of the Formula (IA), (IB), (IC), (ID) and (IE) in which $R_1$ is —$OR_6$ and $R_6$ is $C_1$-$C_5$ straight-chain alkyl groups.

In yet another embodiment, specifically provided are compounds of the Formula (IA), (IB), (IC), (ID) and (IE) in which $R_1$ is —$OR_6$ and $R_6$ is methyl.

In yet another embodiment, specifically provided are compounds of the Formula (IA), (IB), (IC), (ID) and (IE) in which $R_1$ is hydroxyalkyl for example hydroxymethyl.

In yet another embodiment, specifically provided are compounds of the Formula (IA), (IB), (IC) and (ID) in which $R_2$ and $R_3$ are independently selected from hydrogen or $C_1$-$C_5$ straight-chain alkyl groups.

In yet another embodiment, specifically provided are compounds of the Formula (IA), (IB), (IC) and (ID) in which $R_2$ and $R_3$ are independently selected from hydrogen or methyl.

In yet another embodiment, specifically provided are compounds of the Formula (IA), (IB), (IC), (ID) and (IE) in which $R_4$ selected from hydrogen or $C_1$-$C_5$ straight-chain alkyl groups.

In yet another embodiment, specifically provided are compounds of the Formula (IA), (IB), (IC), (ID) and (IE) in which $R_4$ selected from hydrogen or methyl.

In yet another embodiment, specifically provided are compounds of the Formula (IA), (IB), (IC), (ID) and (IE) in which 'n' is selected from 1 or 2.

In yet another embodiment, specifically provided are compounds of the Formula (IA), in which $R_1$ is —$OC(O)R_6$ and $R_6$ is $C_1$-$C_{10}$ straight-chain alkyl groups, In yet another embodiment, specifically provided are compounds of the Formula (IA), in which $R_1$ is —OC(O)—$(CH_2)_8$ $CH_3$.

In one embodiment, specifically provided are compounds of the Formula (IB), in which X is O.

In yet another embodiment, specifically provided are compounds of the Formula (IB), in which X is S.

In yet another embodiment, specifically provided are compounds of the Formula (IB), in which $Am_1$ is Thr.

In yet another embodiment, specifically provided are compounds of the Formula (IB), in which $Am_1$ is Asp.

In yet another embodiment, specifically provided are compounds of the Formula (IB), in which $Am_1$ is Ile.

In yet another embodiment, specifically provided are compounds of the Formula (IB), in which $Am_1$ is Phe.

In yet another embodiment, specifically provided are compounds of the Formula (IB), in which $Am_1$ is Ser.

In yet another embodiment, specifically provided are compounds of the Formula (IB), in which $Am_1$ is Ala.

In yet another embodiment, specifically provided are compounds of the Formula (IB), in which $Am_1$ is Trp.

In yet another embodiment, specifically provided are compounds of the Formula (IB), in which $R_7$ is free alpha carboxylic acid of Thr.

In yet another embodiment, specifically provided are compounds of the Formula (IB), in which $R_7$ is free alpha carboxylic acid of Asp.

In yet another embodiment, specifically provided are compounds of the Formula (IB), in which $R_7$ is free alpha carboxylic acid of Ile.

In yet another embodiment, specifically provided are compounds of the Formula (IB), in which $R_7$ is free alpha carboxylic acid of Phe.

In yet another embodiment, specifically provided are compounds of the Formula (IB), in which $R_7$ is free alpha carboxylic acid of Ser.

In one embodiment, specifically provided are compounds of the Formula (IB), in which $R_7$ is free alpha carboxylic acid of Ala.

In yet another embodiment, specifically provided are compounds of the Formula (IB), in which $R_7$ is free alpha carboxylic acid of Trp.

In yet another embodiment, specifically provided are compounds of the Formula (IB), in which $R_7$ is alpha carboxylic ester of Thr.

In yet another embodiment, specifically provided are compounds of the Formula (IB), in which $R_7$ is alpha carboxylic ester of Thr; wherein, the ester is benzylic ester.

In yet another embodiment, specifically provided are compounds of the Formula (IB), in which $R_7$ is alpha carboxylic amide of Thr; wherein the said amide nitrogen is optionally substituted by amino.

In yet another embodiment, specifically provided are compounds of the Formula (IC), in which $Am_1$ is Thr.

In yet another embodiment, specifically provided are compounds of the Formula (IC), in which $R_8$ is alpha amino group of Thr; wherein the amino group is optionally substituted with —CONH—$C_1$-$C_5$ straight-chain alkyl groups.

In yet another embodiment, specifically provided are compounds of the Formula (IC), in which $R_8$ is alpha amino group of Thr; wherein the amino group is substituted with —CONH-methyl.

In yet another embodiment, specifically provided are compounds of the Formula (IE), in which $R_1'$ is hydrogen.

In yet another embodiment, specifically provided are compounds of the Formula (IE), in which $R_1'$ is $C_1$-$C_5$ straight-chain alkyl groups.

In yet another embodiment, specifically provided are compounds of the Formula (IE), in which $R_1'$ is methyl.

In yet another embodiment, specifically provided are compounds of the Formula (IE), in which both $R_2$ and $R_3$ are hydrogen.

In yet another embodiment, specifically provided are compounds of the Formula (IE), in which both $R_b$ and $R_b'$ together represent an oxo (=O) group.

In yet another embodiment, specifically provided are compounds of the Formula (IE), in which both $R_b$ and $R_b'$ together represent a thioxo (=S) group.

In yet another embodiment, specifically provided are compounds of the Formula (IE), in which both $R_b$ and $R_b'$ represent hydrogen.

In yet another embodiment, specifically provided are compounds of the Formula (IE), in which X is O.

In yet another embodiment, specifically provided are compounds of the Formula (IE), in which X is S.

In yet another embodiment, specifically provided are compounds of the Formula (IE), in which $Am_1$ is Thr.

In yet another embodiment, specifically provided are compounds of the Formula (IE), in which $Am_1$ is Ser.

In yet another embodiment, specifically provided are compounds of the Formula (IE), in which $R_4'$ is hydrogen.

In yet another embodiment, specifically provided are compounds of the Formula (IE), in which $R_4'$ is $C_1$-$C_5$ straight-chain alkyl groups.

In yet another embodiment, specifically provided are compounds of the Formula (IE), in which $R_4'$ is methyl.

In yet another embodiment, specifically provided are compounds of the Formula (IE), in which n is 1.

In yet another embodiment, specifically provided are compounds of the Formula (IE), in which $R_7$ is free alpha carboxylic acid of Thr.

In yet another embodiment, specifically provided are compounds of the Formula (IE), in which $R_7$ is free alpha carboxylic acid of Ser.

In an embodiment, specific compounds of formula (I) without any limitation are enumerated in Table (1):

TABLE 1

| Compound No | Structure |
|---|---|
| 1. | 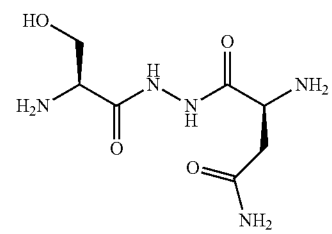 [SMILES: NC(=O)C[C@H](N)C(=O)NNC(=O)[C@@H](N)CO] |
| 2. | 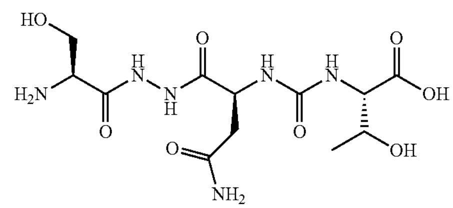 |
| 3. | 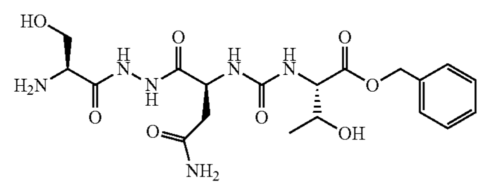 [SMILES: CC(O)[C@H](NC(=O)N[C@@H](CC(N)=O)C(=O)NNC(=O)[C@@H](N)CO)C(=O)OCc1ccccc1] |
| 4. | 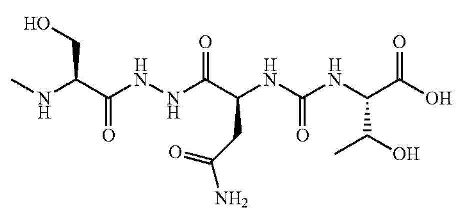 [SMILES: CN[C@@H](CO)C(=O)NNC(=O)[C@H](CC(N)=O)NC(=O)N[C@H](C(=O)O)C(C)O] |
| 5. | 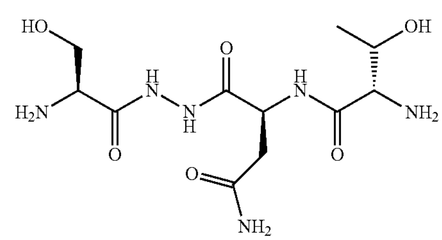 [SMILES: CC(O)[C@H](N)C(=O)N[C@@H](CC(N)=O)C(=O)NNC(=O)[C@@H](N)CO] |
| 6. | 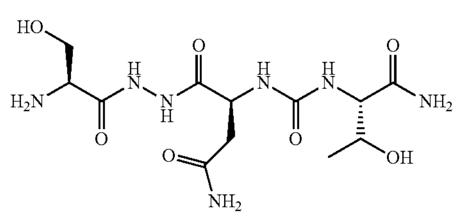 [SMILES: CC(O)[C@H](NC(=O)N[C@@H](CC(N)=O)C(=O)NNC(=O)[C@@H](N)CO)C(N)=O] |

TABLE 1-continued

| Compound No | Structure |
|---|---|
| 7. | [structure of Ser-azaAsn-ureido-Asp] |
| 8. | [structure of Ser-azaAsn-ureido-Ile] |
| 9. | [structure of Ser-azaAsn-ureido-Phe] |
| 10. | [structure of Ser-azaAsn-ureido-Thr methyl ester] |
| 11. | [structure of O-methyl-Ser-azaAsn-ureido-Thr] |
| 12. | [structure of Thr-azaAsn-ureido-Ser] |
| 13. | [structure of Thr-azaAsn-ureido-Ser] |
| 14. | [structure of Ser-azaAsn-ureido-Thr] |
| 15. | [structure of Ser-azaAsn-ureido-Thr] |
| 16. | [structure of Ala-azaAsn-ureido-Thr] |
| 17. | [structure of Ser-azaAsn-ureido-Ala] |
| 18. | [structure of Ser-azaAsn-Thr-ureido-N-methyl] |
| 19. | [structure with diaminomethyl-azaAsn-ureido-Thr] |
| 20. | [structure of Ser-N-methyl-azaAsn-ureido-Thr] |

TABLE 1-continued

| Compound No | Structure |
|---|---|
| 21. | (structure) |
| 22. | (structure) |
| 23. | (structure) |
| 24. | (structure) and |
| 25. | (structure) | stereoisomer thereof or a pharmaceutically acceptable salt thereof.

In one embodiment, the present invention provided a pharmaceutical composition comprising the compound as disclosed, and a pharmaceutically acceptable carrier or diluent.

The compounds as disclosed in the present invention are formulated for pharmaceutical administration.

In one embodiment, the present invention provides use of the compounds as disclosed in the present invention for the preparation of a medicament for the treatment of cancer.

In one embodiment, the present invention provides use of the compounds as disclosed in the present invention for the preparation of a medicament for the treatment of bacterial, viral and fungal infections.

In one embodiment, the present invention provides a method of treatment of cancer, wherein the method comprises administration of an effective amount of the compound of the present invention to the subject in need thereof.

In one embodiment, the present invention provides a method for inhibiting growth of tumour cells and/or metastasis by administering an effective amount of the compound of the present invention to the subject in need thereof.

The said tumour cells include cancer such as but not limited to melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

Still yet another embodiment of the present invention provides a method of treatment of infection via immunopotentiation caused by inhibition of immunosuppressive signal induced by PD-1, PD-L1, or PD-L2, wherein the method comprises administration of an effective amount of the compound of the present invention to the subject in need thereof.

The infectious disease includes but not limited to HIV, Influenza, Herpes, *Giardia*, Malaria, *Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria chlamydia, rickettsial bacteria, *mycobacteria, staphylococci, streptococci, pneumonococci, meningococci* and *conococci, klebsiella, proteus, serratia, pseudomonas, E. coli, legionella,* diphtheria, *salmonella, bacilli,* cholera, tetanus, botulism, anthrax, plague, leptospirosis, and Lyme's disease bacteria, pathogenic infection by the fungi *Candida (albicans, krusei, glabrata, tropicalis,* etc.), *Cryptococcus neoformans, Aspergillus (fumigatus, niger,* etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum,* and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

The compounds of the present invention may be used as single drugs or as a pharmaceutical composition in which the compound is mixed with various pharmacologically acceptable materials.

The pharmaceutical composition is usually administered by a parenteral administration route, but can be administered by oral or inhalation routes. Examples of the parenteral administration includes but not limited to intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration.

The dosage of the compounds of the present invention varies depending on age, weight, symptom, therapeutic efficacy, dosing regimen and/or treatment time. Generally, they may be administered by a parenteral route (preferably intravenous administration) in an amount of 1 mg to 100 mg per time, from once a couple of days, once 3 days, once 2 days, once a day to a couple of times a day, in the case of an adult, or continuously administered by intravenous administration from 1 to 24 hours a day. Since the dosage is affected by various conditions, an amount less than the above dosage may sometimes work well enough, or higher dosage may be required in some cases.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the compounds of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the compound of the present invention.

The compound of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, it can be used with a cancer treatment adjunct, such as a leucopenia (neutropenia) treatment drug, thrombocytopenia treatment drug, antiemetic and cancer pain intervention drug, concomitantly or in a mixture form.

The compound of the present invention can be used with other immunomodulators concomitantly or in a mixture form. Examples of the immunomodulator include various cytokines. Examples of the cytokines that stimulates immune responses include GM-CSF, M-CSF, G-CSF, interferon-α, β, or γ, IL-1, IL-2, IL-3 and IL-12.

Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein, the term 'compound(s)' or 'peptidomimetics' or "peptidomimetic compounds' comprises the compounds disclosed in the present invention.

As used herein, the term "comprise" or "comprising" is generally used in the sense of include, that is to say permitting the presence of one or more features or components.

As used herein, the term "including" as well as other forms, such as "include", "includes," and "included," is not limiting.

As used herein, the term "optionally substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

As used herein, the term "Aliphatic" means alkyl, alkenyl or alkynyl as defined herein. As used herein, the term "alkyl" refers to saturated aliphatic groups, including $C_1$-$C_{20}$ straight-chain alkyl groups, $C_1$-$C_{10}$ straight-chain alkyl groups, $C_1$-$C_5$ straight-chain alkyl groups, $C_1$-$C_{20}$ branched-chain alkyl groups, $C_1$-$C_{10}$ branched-chain alkyl groups or $C_1$-$C_5$ branched-chain alkyl groups.

As used herein, the term "acyl" refers to RC(O)—, wherein R is alkyl as defined above. Examples of acyl group include, but are not limited to acetyl, —C(O)(CH$_2$)$_4$—CH$_3$, —C(O)(CH$_2$)$_6$CH$_3$ and —C(O)(CH$_2$)$_8$CH$_3$ As used herein, the term "Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain that may be straight or branched. Examples of alkenyl group include, but are not limited to ethenyl, propenyl, n-butenyl, i-butenyl, 3-methylbut-2-enyl, n-pentenyl, heptenyl, octenyl, cyclohexylbutenyl and decenyl. "Substituted alkenyl" means an alkenyl group as defined above which is substituted with one or more "aliphatic group substituents" (preferably 1 to 3) which may be the same or different and are as defined herein. Examples of alkenyl aliphatic group substituents include, but are not limited to halo and cycloalkyl groups.

As used herein, the term "Alkoxy" means an alkyl-O— group wherein the alkyl group is as herein described. Examples of alkoxy groups include, but are not limited to methoxy, ethoxy, n-propoxy, i-propoxy, n-butoxy and heptoxy.

As used herein, the term "Alkylthio" means an alkyl-S— group wherein the alkyl group is as herein described. Examples of alkylthio groups include, but are not limited to methylthio, ethylthio, i-propylthio and heptylthio.

As used herein, the term "Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain that may be straight or branched. The alkynyl group may be substituted by one or more halo. Examples of alkynyl groups include, but are not limited to ethynyl, propynyl, n-butynyl, 2-butynyl, 3-methylbutynyl, n-pentynyl, heptynyl, octynyl and decynyl. "Substituted alkynyl" means alkynyl as defined above which is substituted with one or more "aliphatic group substituents" (preferably 1 to 3) which may be the same or different, and are as defined herein.

As used herein the term "amide form" refers to primary, secondary and/or tertiary amides and may be represented by the formula —C(O)NR$_x$R$_y$, wherein R$_x$ may be hydrogen and R$_y$ may be hydrogen, hydroxyl or amino.

As used herein, the term "Amino acid residue refers to natural and unnatural amino acids and can include D- and L-form. Optional substituent on amino acid means replacement of one or more hydrogen radicals in a given structure with the radical of a specified substituent, in case of amino acid containing hydroxyl group such as Serine or Threonine, the hydroxyl group can be substituted with the specified substituent.

As used herein the term "aryl" refers to C$_4$-C$_{10}$ carbocyclic aromatic system containing one or two rings wherein such rings may be fused. Examples of aryl groups include, but are not limited to phenyl and naphthyl.

As used herein the term "arylalkyl" refers to an aryl group as defined above directly bonded to an alkyl group (e.g., benzyl and the like).

As used herein, the term "Aryloxy" means an aryl-O— group wherein the aryl group is as defined above. Examples of aryloxy groups include, but are not limited to phenoxy and 2-naphthyloxy.

As used herein, the term "Aryloxycarbonyl" means an aryl-O—C(O)— group wherein the aryl group is as defined above. Examples of aryloxycarbonyl groups include, but are not limited to phenoxycarbonyl and naphthoxycarbonyl.

As used herein, the term "Arylthio" means an aryl-S— group wherein the aryl group is as described above. Examples of arylthio groups include, but are not limited to phenylthio and naphthylthio.

As used herein, the term "Coupling agent" means a compound that reacts with the hydroxyl moiety of a carboxy moiety thereby rendering it susceptible to nucleophilic attack. Coupling agents of this type are known in the art and include, but are not limited to, EDCI, HATU, HOBt, DIC and DCC.

As used herein the term "ester" refers to (C$_1$-C$_6$) linear or branched alkyl, (C$_4$-C$_{10}$)aryl, (C$_4$-C$_{10}$)heteroaryl or arylalkyl esters;

As used herein, the terms "halogen" or "halo" includes fluorine, chlorine, bromine or iodine.

As used herein the term "heteroaryl" refers to aryl group as defined above containing at least one to four heteroatom selected from N, S or O.

As used herein, the term "Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferably, the ring system contains from 1 to 3 heteroatoms. Preferred ring sizes of rings of the ring system include about 5 to about 6 ring atoms; and such preferred ring sizes are also referred to as "lower". Encompassed by heterocyclyl are fused arylheterocyclyl and fused heteroarylheterocyclyl as defined herein when bonded through the heterocyclyl moiety thereof. The designation of the aza, oxa or thia as a prefix before heterocyclyl define that at least a nitrogen, oxygen or sulfur atom is present respectively as a ring atom. "Substituted heterocyclyl" means a heterocyclyl group as defined above which is substituted with one or more "ring group substituents" (preferably 1 to 3) which may be the same or different and are as defined herein The nitrogen atom of an heterocyclyl may be a basic nitrogen atom. The nitrogen or sulfur atom of the heterocyclyl may also be optionally oxidized to the corresponding N-oxide, S-oxide or S,S-dioxide. Examples of monocyclic heterocyclyl rings include, but are not limited to piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl and tetrahydrothiopyranyl.

As used herein, the term "Hydrate" means a solvate wherein the solvent molecule(s) is/are H$_2$O.

As used herein the term "Hydroxylalkyl" or "Hydroxyalkyl" refers to an alkyl group, as defined above, wherein one or more of the alkyl group's hydrogen atoms have been replaced with hydroxyl groups. Examples of hydroxyalkyl groups include but are not limited to —CH$_2$OH, —CH$_2$CH$_2$OH, —CH$_2$CH$_2$CH$_2$OH, —CH$_2$CH(OH)CH$_2$OH, —CH$_2$CH(OH)CH$_3$ and —CH(CH$_3$)CH$_2$OH.

As used herein the term "Hydroxy" or "Hydroxyl" refers to —OH group.

As used herein the term "Oxo" refers to =O group and thioxo refers to =S group.

As used herein the term "Cyano" refers to —CN group.

As used herein the term "Amino" refers to —NH$_2$ group. Unless set forth or recited to the contrary, all amino groups described or claimed herein may be substituted or unsubstituted.

As used herein the term "Carboxylic acid" refers to —COOH group.

As used herein, the term "amino acid" refers to amino acids having L or D stereochemistry at the alpha carbon.

"Pharmaceutically acceptable salt" is taken to mean an active ingredient, which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "stereoisomers" refers to any enantiomers, diastereoisomers, or geometrical isomers of the compounds of formula (I), wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

Throughout the description and claims the three letter code for natural amino acids are used for example 'Ser' for Serine; 'Asp' for Aspartic acid; 'Ala' for Alanine, 'Ile' for Isoleucine; 'Phe' for Phenylalanine; 'Glu' for Glutamic acid; 'Asn' for Asparagine, 'Trp' for Tryptophan and 'Thr' for Threonine.

The abbreviations used in the entire specification may be summarized herein below with their particular meaning.

° C. (degree Celsius); δ (delta); % (percentage); $Ag_2CO_3$ (Silver carbonate); AcOH (Acetic acid); ACN (Acetonitrile); $Ac_2O$ (Acetic anhydride); brine (NaCl solution); Br or $Br_2$ (Bromine); BnBr (Benzyl bromide); t-BuOH (tert-butanol); $(BoC)_2O$ (Di tert-butyl dicarbonate); bs or brs (Broad singlet); Bzl (Benzyl); CuI (Cuprous iodide); Cbz (Carboxybenzyl), CDI (Carbonyl diimidazole); $CDCl_3$ (Deuteriated chloroform); $CH_2Cl_2$/DCM (Dichloromethane); $Cs_2CO_3$ (Cesium carbonate); $CCl_4$ (Carbon tetrachloride); $CBr_4$ (Carbon tetrabromide); $CH_3SO_2Cl$/$MeSO_2Cl$ (Methanesulfonyl chloride); $CH_2N_2$ (Diazomethane); DMF (Dimethyl formamide); DMA (Dimethyl acetamide); DMSO (Dimethyl sulphoxide); DME (Dimethoxy ethane); DIPEA/DIEA (N,N-Diisopropyl ethylamine); DMAP (Dimethyl amino pyridine); DCE (Dichloro ethane); DCC (Dicyclohexylcarbodiimide); DIC(N,N'-diisopropylcarbodiimide); DMSO-$d_6$ (Deuterated DMSO); d (Doublet); dd (Doublet of doublets); dt (Doublet of triplets); EDC.HCl (1-(3-Dimethyl aminopropyl)-3-carbodiimide hydrochloride); EtOH (Ethanol); $Et_2O$ (Diethyl ether); EtOAc (Ethyl acetate); ECF (ethylchloroformate); Fe (Iron powder); g or gr (gram); H or $H_2$ (Hydrogen); $H_2O$ (Water); HOBt (1-Hydroxy benzotriazole); $H_2SO_4$ (Sulphuric acid); HBr (Hydrobromic acid); HCl (Hydrochloric acid); h or hr (Hours); HATU (2-(1H-7-Azabenzotriazol-1-yl)-1,1, 3,3-tetramethyl uranium hexafluoro phosphate methanaminium); Hz (Hertz); HPLC (High-performance liquid chromatography); $I_2$ (Iodine); J (Coupling constant); $K_2CO_3$ (Potassium carbonate); $K_3PO_4$ (Potassium phosphate); $KH_2PO_4$ (Mono potassium phosphate); KOBu$^t$ (Potassium tert-butoxide), LDA (Lithium diisopropylamide); LAH (Lithium aluminium hydride); LiOH.$H_2O$ (Lithium hydroxide mono hydrate); LiHMDS (Lithium bis(trimethylsilyl)amide); LCMS (Liquid chromatography mass spectroscopy); MeOH/$CH_3OH$ (Methanol); MeI (Methyl iodide); MP (Melting point); mmol (Millimoles); M (Molar); μl (Micro liter); mL (Milliliter); mg (Milligram); m (Multiplet); mm (Millimeter); MHz (Megahertz); MS (ES) (Mass spectroscopy-electro spray); min (Minutes); NaOBu$^t$ (Sodium tert-butoxide); NaOCH$_3$ (Sodium methoxide); NaOAc (Sodium acetate); NaOH (Sodium hydroxide); NMM (N-methyl morpholine); $NH_2NH_2.H_2O$ (Hydrazine hydrate); ($NaBH_4$ (Sodium borohydride); $NaCNBH_3$ (Sodium cyanoborohydride); NaH (Sodium hydride); $Na_2SO_4$ (Sodium sulphate); $N_2$ (Nitrogen); NMR (Nuclear magnetic resonance spectroscopy); $NH_4Cl$ (Ammonium chloride); $NH_3$ (Ammonia); $Na_2CO_3$ (Sodium carbonate); $NH_2OH.HCl$ (Hydroxylamine hydrochloride; 10% Pd/C (10% palladium activated carbon); $PBr_3$ (Phosphorous tribromide); PPA (Polyphosphoric acid); $P_2O_5$ (Phosphorus pentoxide); $SOCl_2$ (Thionyl chloride); S (Singlet); TEA/$Et_3N$ (Triethyl amine); TFA (Trifluoroaceticacid); TLC (Thin Layer Chromatography); THF (Tetrahydrofuran); TIPS (Triisopropyl silane); Ti($^i$Opr)$_4$ (Titanium tetra isopropoxide); TFA/$CF_3COOH$ (Trifluoro acetic acid); t (Triplet); etc.

EXPERIMENTAL

An embodiment of the present invention provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention The starting materials are generally available from commercial sources such as Sigma-Aldrich, USA or Germany; Chem-Impex USA; G.L. Biochem, China and Spectrochem, India.

Purification and Characterization of Compounds

Analytical HPLC was performed using on ZIC HILIC 200A column (4.6 mm×250 mm, 5 μm), Flow rate: 1.1 mL/min. The elution conditions used are:

Method 1: Buffer A: 10 mmol ammonium acetate, Buffer B: Acetonitrile, Equilibration of the column with 90% buffer B and elution by a gradient of 90% to 40% buffer B during 20 min.

Method 2: Buffer A: 10 mmol ammonium acetate, Buffer B: Acetonitrile, Equilibration of the column with 90% buffer B and elution by a gradient of 90% to 10% buffer B during 20 min.

LCMS was performed on API 2000 LC/MS/MS triple quad (Applied biosystems) with Agilent 1100 series HPLC with G1315 B DAD or using Agilent LC/MSD VL single quad with Agilent 1100 series HPLC with G1315 B DAD, or using Shimadzu LCMS 2020 single quad with Prominence UFLC system with SPD-20 A DAD.

Example 1

Synthesis of Compound 1

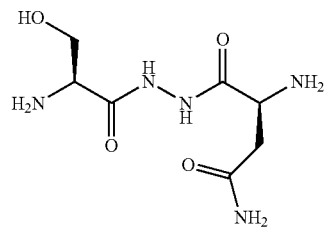 [SMILES: NC(=O)C[C@H](N)C(=O)NNC(=O)[C@@H](N)CO]

Step 1:

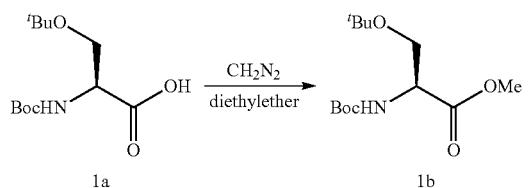 [SMILES: CC(C)(C)OC[C@H](NC(=O)OC(C)(C)C)C(=O)O ; "CH2N2" ; COC(=O)[C@H](COC(C)(C)C)NC(=O)OC(C)(C)C]

Diazomethane in diethyl ether (generated from 8 g of N-Nitroso-N-methylurea in 50% aqueous KOH) was added under nitrogen atmosphere to the solution of compound 1a (6 g, 23.0 mmol) in MeOH (60 mL) at 0° C. and the reaction was stirred at room temperature for 30 min. The reaction was monitored by TLC. After completion of the reaction, the reaction mixture was concentrated under reduced pressure to yield 5.9 g of pure compound 1b (Yield: 93%).

LCMS: 220.1 [(M-O$^t$Bu)+H]$^+$, 298.2 (M+Na)$^+$.

Step 2:

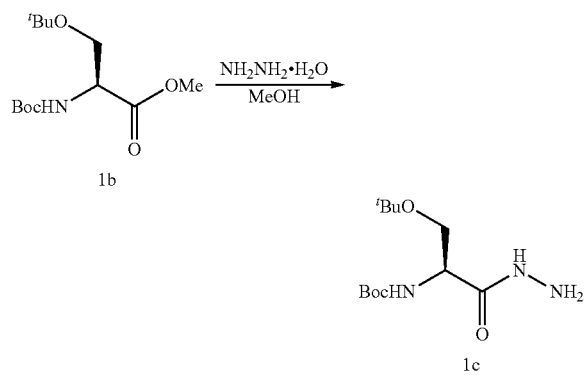

99% Hydrazine hydrate (1 mL) was added to a solution of intermediate 1b (1.0 g, 3.6 mmol) in methanol (10 mL) and stirred at room temperature for 12 h. The completeness of the reaction was confirmed by TLC analysis. The reaction mixture was evaporated under reduced pressure to yield 0.75 g of pure compound 1c (Yield: 75.0%)

LCMS: 276.3 (M+H)$^+$.

Step 3:

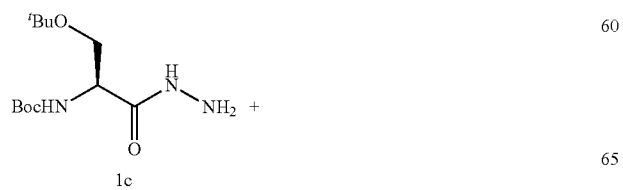

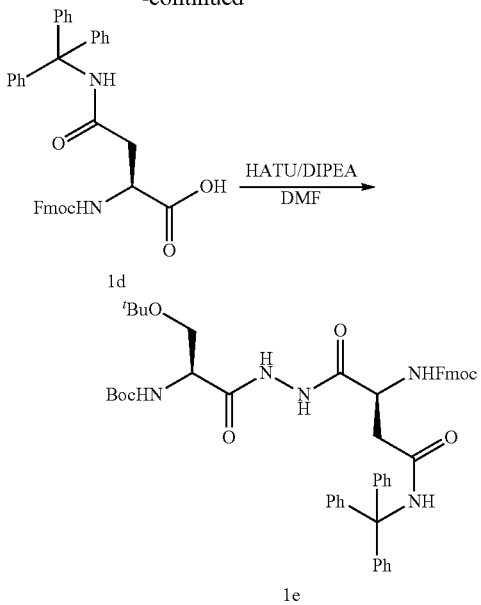

Active ester of compound was prepared by treating intermediate 1d (0.2 g, 0.33 mmol) with HATU/DIPEA method in DMF (5 mL) (0.14 g, 0.37 mmol of HATU and 0.09 g, 0.7 mmol of DIPEA). After 10 minutes intermediate 1c (0.09 g, 0.33 mmol) was added to the active ester and stirred at room temperature for 12 h. The completeness of the reaction was confirmed by TLC analysis. The reaction mixture was then partitioned between ice water and ethyl acetate. Organic layer was washed with brine, dried over Na$_2$SO$_4$ and evaporated under reduced pressure to yield compound 1e, which was further purified by silica gel column chromatography (Eluent: 0-5% methanol in chloroform) to yield 0.2 g of pure compound 1e (Yield-70%)

LCMS: 854.2 (M+H)$^+$.

Step-4:

Fmoc group of 1e was de-protected by the addition of diethyl amine (3 mL) to 1e (2 g, 0.67 mmol) in CH$_2$Cl$_2$ (3 mL). The reaction mixture was stirred at room temperature for 30 min. After completion of the reaction (monitored by TLC), the resulting solution was concentrated in vacuum to yield a thick gummy residue. The residue was further washed with diethyl ether/hexane (1:1) to yield 0.8 g of compound 1f. LCMS: 632.5 (M+H)$^+$.

Step 5:

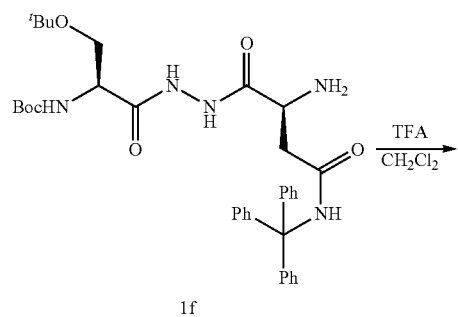

To a stirred solution of intermediate if (1.2 g) in CH$_2$Cl$_2$ (10 mL), Trifluoro aceticacid (10 mL) and catalytic amount of tri isopropyl silane were added and stirred for 3 h at room temperature to remove the acid sensitive protecting groups. The resulting solution was concentrated in vacuum to yield 0.5 g of crude compound 1. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 m L/min. The compound was eluted by gradient elution 0-2 min=90% buffer B, 2-23 min=90-5% buffer B with a flow rate of 20 mL/min. HPLC: (method 2): RT −18.26 min. LCMS: 235.3 (M+2H)$^+$.

Example 2

Synthesis of Compound 2

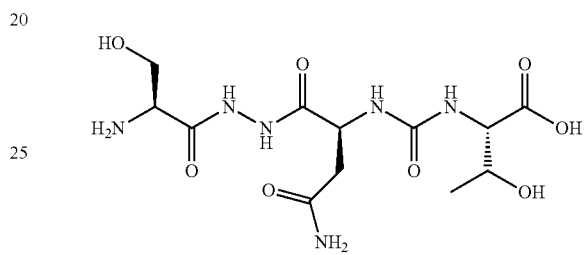

Method A:
Step 1a:

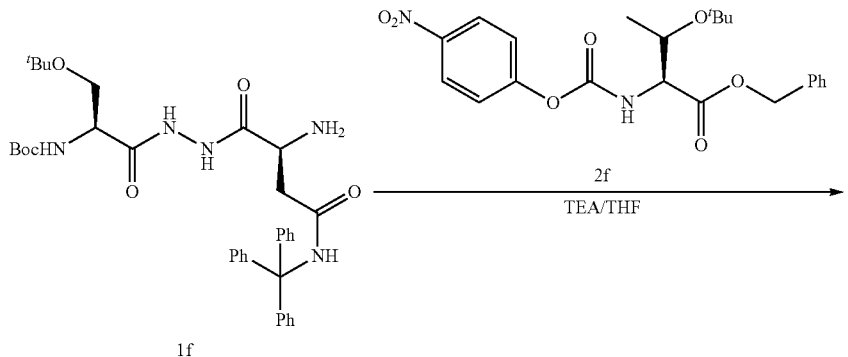

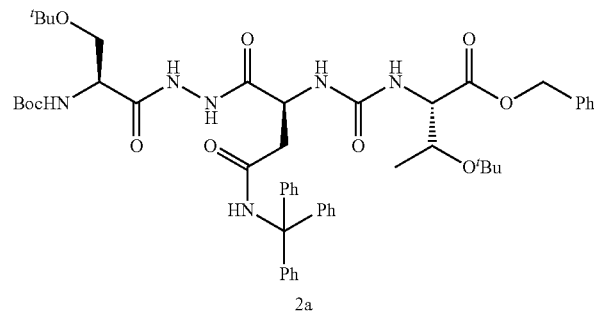

The urea linkage was carried out using coupling of compound 1f (5 g, 7.9 mmol) in THF (25 mL) at room temperature, with compound 2f (3.36 g, 9.5 mmol). The coupling was initiated by the addition of TEA (1.6 g, 15.8 mmol) in THF (25 mL) and the resultant mixture was stirred at room temperature. After the completion of 20 h, THF was evaporated from the reaction mass, and partitioned between water and ethyl acetate. Organic layer was washed with water, brine, dried over $Na_2SO_4$ and evaporated under reduced pressure to yield compound 2a, The residue was further washed with diethyl ether/hexane (7:3) to yield 3.0 g of compound 2a. LCMS: 923.8 $(M+H)^+$.

Step 2a:

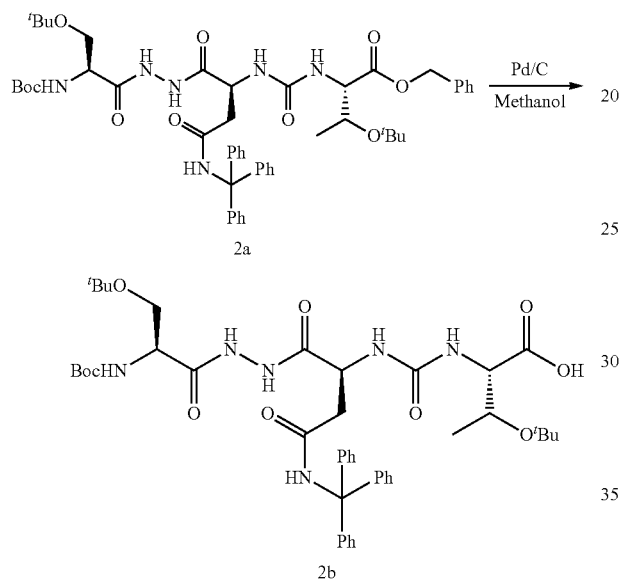

To a solution of intermediate 2a (0.5 g) in methanol (10.0 mL) under inert atmosphere, was added 10% Pd—C (0.1 g) and the mixture was stirred at room temperature for 1 h under $H_2$ atmosphere. The completion of the reaction was confirmed by TLC analysis. The Pd—C catalyst was then removed by filtration through a celite pad, which was then washed with 20 mL of methanol. The combined organic filtrate was evaporated under reduced pressure to get the desired 0.45 g compound 2b in quantitative yield.

LCMS: 833.6 $(M+H)^+$.

Step 3a:

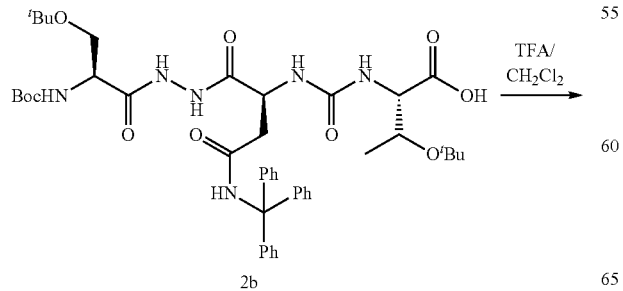

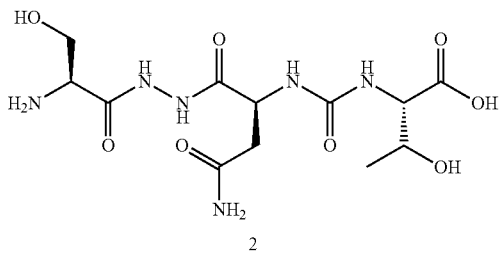

To a solution of intermediate 2b (0.22 g, 0.3 mmol) in $CH_2Cl_2$ (5 mL), trifluoro acetic acid (5 mL) and catalytic amount of tri isopropyl silane were added and stirred for 3 h at room temperature. The resulting solution was concentrated in vacuum to yield 0.2 g of compound 2. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min. The compound was eluted by gradient elution 0-3 min=90% buffer B, 3-20 min=90-40% buffer B with a flow rate of 20 mL/min. HPLC: (method 2) RT −14.5 min. LCMS: 379.0 $(M+H)^+$.

Synthesis of compound 2f, p-nitro phenyl carbamate $(NO_2—C6H4-OCO-Thr(O^tBu)-Bzl,)$

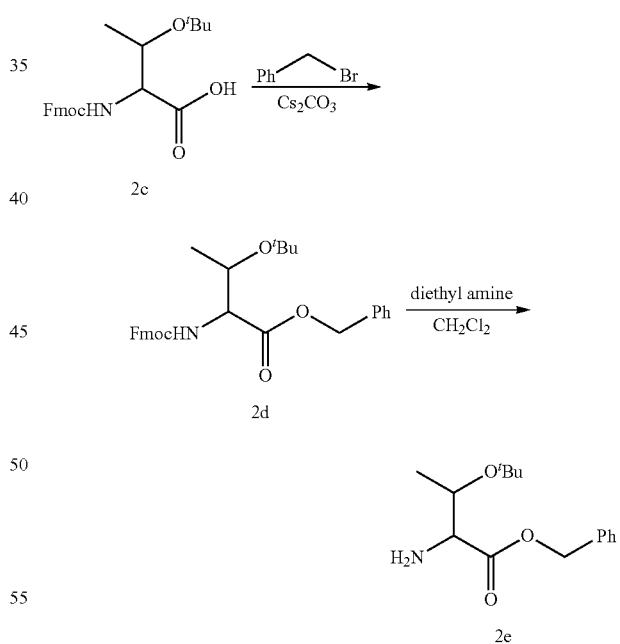

To a solution of compound 2c (15.0 g, 37.7 mmol) in 100.0 mL of DMF, $Cs_2CO_3$ (14.8 g, 45.2 mmol) was added and the resulting mixture was cooled to 0° C. To the cooled reaction mixture benzyl bromide (7.74 g, 345.2 mmol) was added and the solution was stirred for 30 min at ice cold temperature and then at room temperature for 12 h. The reaction mixture was further concentrated under reduced pressure and diluted with ethyl acetate (150 mL). The organic layer was washed with water (2×100 mL), brine (1×100 mL) and dried over $Na_2SO_4$.

The filtered solution was concentrated and purified by silica gel column chromatography (Eluent: 0-30% ethyl acetate in Hexane) to yield 18.5 g of compound 2d as a white solid. LCMS: 433.1 (M-O'Bu+H)+, 397.2 (M-OBzl)+).

Fmoc group on intermediate 2d was deprotected by adding diethyl amine (40.0 mL) to intermediate 2d (10.0 g, 20.5 mmol) in CH$_2$Cl$_2$ (40.0 mL) for 1 h with stirring at room temperature. The resulting solution was concentrated in vacuum and the thick-residue was purified by column chromatography over neutral alumina (Eluent: 0-50% ethyl acetate in hexane then 0-5% methanol in chloroform) to yield 3.9 g of compound 2e (Yield: 72%)

LCMS: 266.5 (M+H)+.

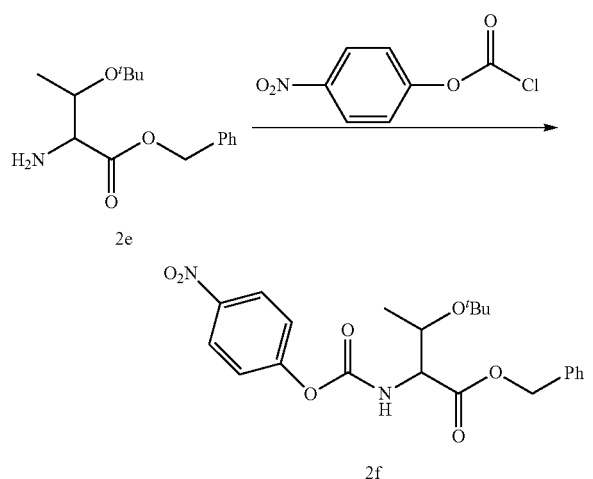

To a stirred solution of intermediate 2e (1.6 g, 6.0 mmol) in CH$_2$Cl$_2$ (30 mL), TEA (1.2 g, 12.0 mmol) was added and the solution was stirred at room temperature for 5-10 min. Then a solution of 4-nitrophenyl chloroformate (1.3 g, 6.6 mmol) in CH$_2$Cl$_2$ (10 mL) was added and the resultant mixture was stirred at room temperature for 12 h. The completion of the reaction was confirmed by TLC analysis (Ref. Int. J. Pept. Protein Res. 1995, 46, 434). After completion of reaction, the reaction mixture was diluted with CH$_2$Cl$_2$ (50 mL) and washed with 1.0 M of Sodium bi sulphate (50 mL×2) and 1.0 M Sodium carbonate (50 mL×2), dried over Na$_2$SO$_4$ and evaporated under reduced pressure to yield crude compound 2f, which was further purified by silica gel column chromatography (eluent: 0-20% ethyl acetate in Hexane) to yield 0.8 g of compound 2f. $^1$H NMR (DMSO-d$_6$, 300 MHz): δ 1.04 (s, 9H), 1.16 (d, 3H), 4.11 (m, 1H), 5.11 (m, 3H), 6.91 (d, 2H), 7.40 (m, 5H), 8.10 (d, 2H), 8.26 (br, 1H).

Method B: Alternate Method for Synthesis of Compound 2

Step 1b:

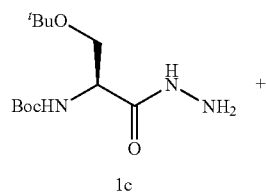

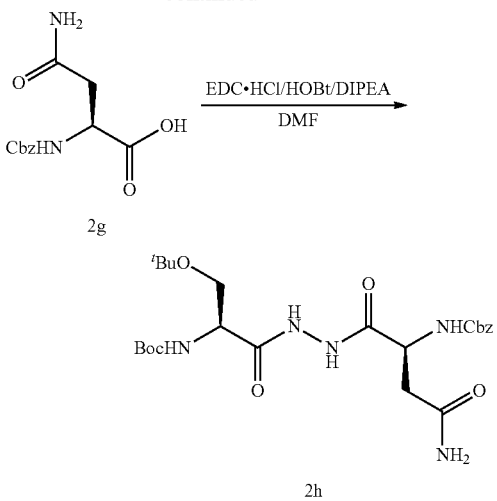

DIPEA (16.9 g, 130.8 mmol) was added slowly to a stirred solution of 2 g (11.6 g, 43.6 mmol) and HOBt (7.1 g, 52.3 mmol) in DMF (100 mL). The reaction mixture was stirred at room temperature for 5 min. To the above reaction mixture compound 1c was added slowly and stirred at room temperature for 12 h. The completeness of the reaction was confirmed by TLC analysis. The reaction mixture was then quenched with ice to get precipitate, filtered the solid and re-crystallized with CH$_2$Cl$_2$ to yield 8 g of compound 2 h, which was directly used for the next step.

Step 2b:

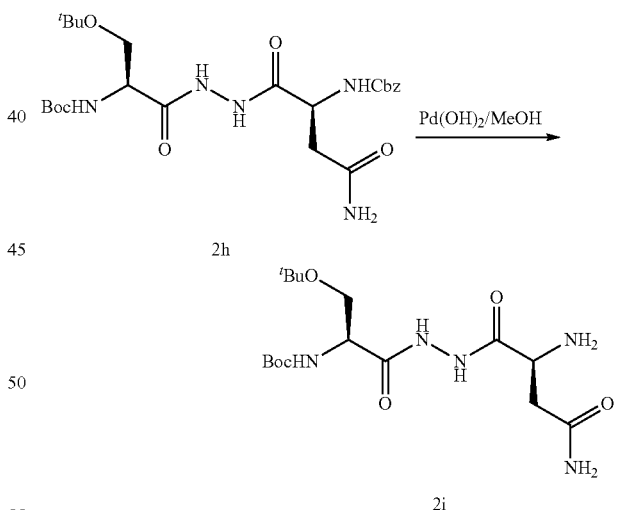

To a solution of compound 2 h (8.0 g) in methanol (80.0 mL) under inert atmosphere, was added 10% Pd(OH)$_2$ (2.0 g) and the mixture was stirred for 8 h under H$_2$ atmosphere. The completion of the reaction was confirmed by TLC analysis. The Pd(OH)$_2$ catalyst was then removed by filtration through a celite pad, which was then washed with 100 mL of methanol. The combined organic filtrate on evaporation under reduced pressure to yield crude compound which was further washed with diethyl ether to yield 3.8 g of compound 2i, which was directly used for the next step.

Step 3b:

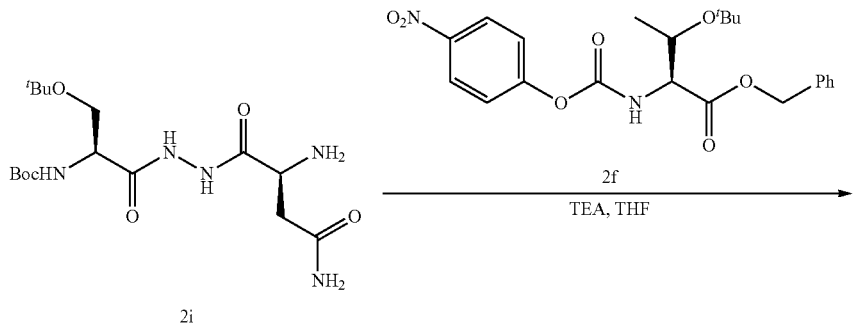

The urea linkage was carried out using coupling of compound 2i (4.5 g, 11.6 mmol) in THF (25 mL) at room temperature, with compound 2f (5.9 g, 13.9 mmol). The coupling was initiated by the addition of TEA (2.3 g, 23.1 mmol) in THF (25 mL) and the resultant mixture was stirred at room temperature. After the completion of 20 h, THF was evaporated from the reaction mass, and partitioned between water and ethyl acetate. Organic layer was washed with water, brine, dried over $Na_2SO_4$ and evaporated under reduced pressure to yield crude compound which was further washed with diethyl ether to yield 3.2 g of compound 2j. LCMS: 681.95 $(M+H)^+$.

Step 4b:

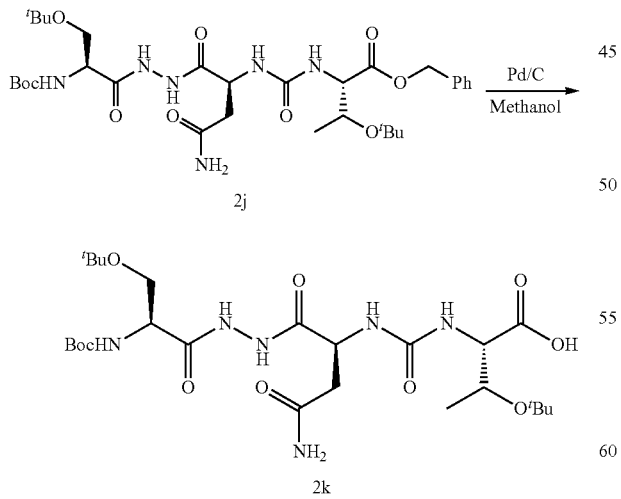

To a solution of intermediate 2j (3.2 g) in methanol (30.0 mL) under inert atmosphere, was added 10% Pd—C (1.0 g) and the mixture was stirred at room temperature for 1 h under $H_2$ atmosphere. The completion of the reaction was confirmed by TLC analysis. The Pd—C catalyst was then removed by filtration through a celite pad, which was then washed with 40 mL of methanol. The combined organic filtrate was evaporated under reduced pressure to get the desired 2.8 g of compound 2k in quantitative yield. LCMS: 591.0 $(M+H)^+$.

Step 5b:

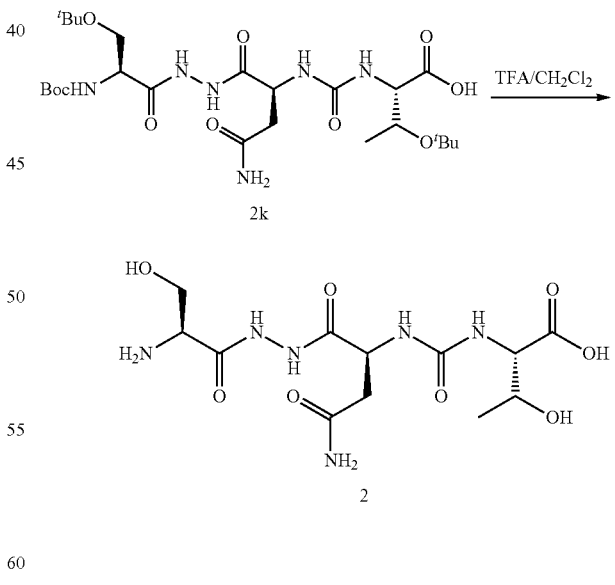

To a solution of intermediate 2k (2.8 g, 4.7 mmol) in $CH_2Cl_2$ (10 mL), trifluoro acetic acid (10 mL) and catalytic amount of tri isopropyl silane were added and stirred for 3 h at room temperature. The resulting solution was concentrated in vacuum to yield 2.0 g of compound 2.

LCMS: 379.2 $(M+H)^+$.

Example 3

Synthesis of Compound 3

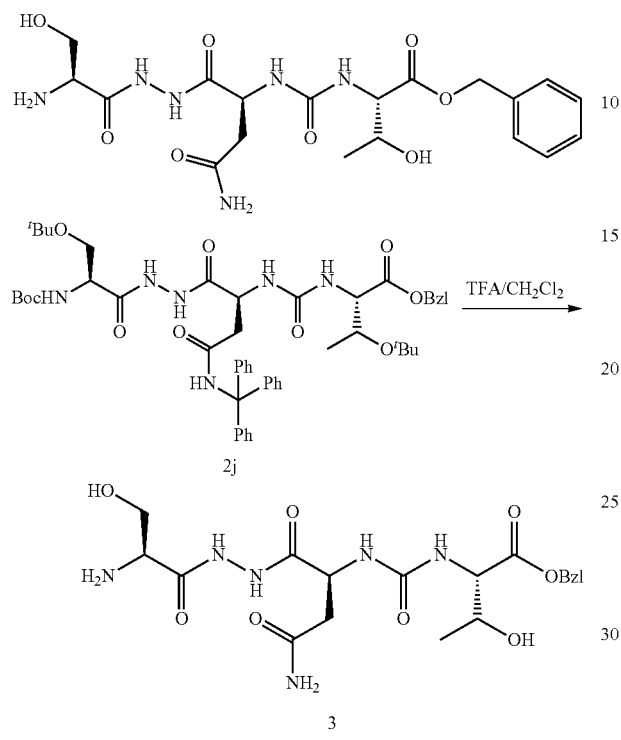

To a stirred solution of intermediate 2j (0.92 g, 1.0 mmol) in $CH_2Cl_2$ (5 mL), Trifluoro aceticacid (5 mL) and catalytic amount of tri isopropyl silane were added and stirred for 3 h at room temperature to remove the acid sensitive protecting groups. The resulting solution was concentrated in vacuum to yield 0.3 g of compound 3 as a crude solid. LCMS: 469.1 $(M+H)^+$.

Example 4

Synthesis of Compound 4

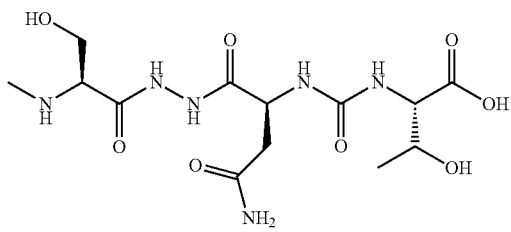 [SMILES: CN[C@@H](CO)C(=O)NNC(=O)[C@H](CC(N)=O)NC(=O)N[C@H](C(=O)O)C(C)O]

The compound was synthesised using similar procedure as exemplified in (example 2, method B) using N-Boc-N-methyl-Ser(O$^t$Bu)-OH in step 1 of example 1 instead of N-Boc-Ser(OtBu)—OH to yield 0.25 g crude material of the title compound. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-20 min=90-40% buffer B with a flow rate of 20 mL/min. HPLC: (Method 2): RT –14.4 min. LCMS: 393.0 $(M+H)^+$.

Example 5

Synthesis of Compound 5

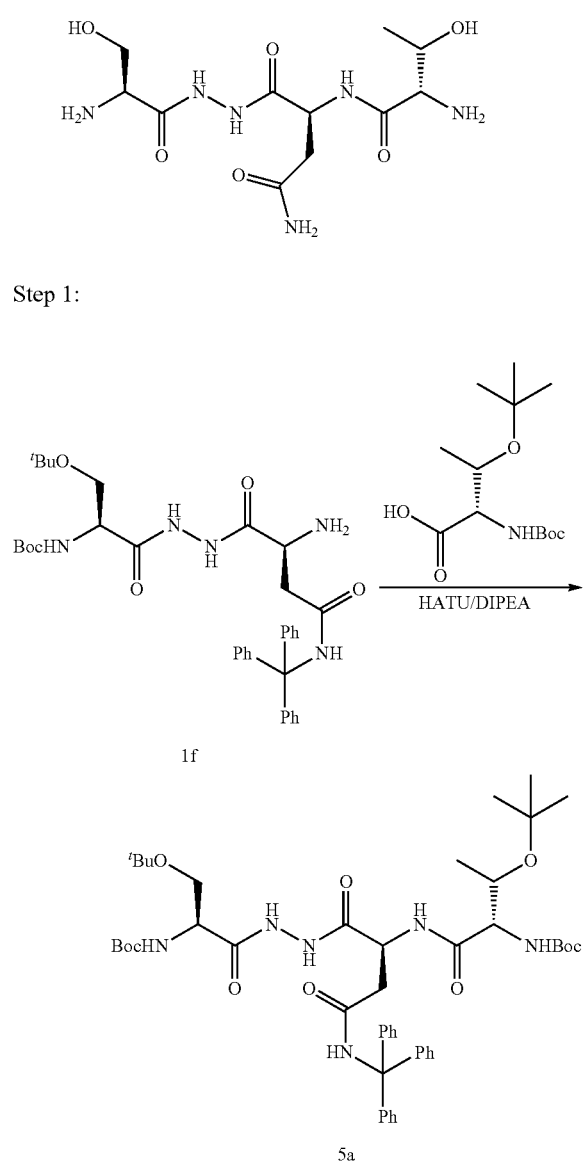

Step 1:

Active ester of Boc-Thr(O$^t$Bu)-OH (0.15 g, 0.54 mmol) was prepared using HATU/DIPEA method in DMF (HATU: 0.24 g, 0.64 mmol and DIPEA: 0.14 g, 1.08 mmol). To this mixture, intermediate-1f (0.35 g, 0.54 mmol) was added and stirred at room temperature for 6 h. The progress of the reaction was monitored by TLC. On completion of the starting materials as monitored by TLC, the reaction mixture was partitioned between ice water and ethyl acetate. Organic layer was washed with brine, dried over $Na_2SO_4$ and evaporated under reduced pressure to yield crude compound. The crude residue was further washed with diethyl ether/hexane (7:3) to yield 0.47 g of compound 5a. LCMS: 911.4 $(M+Na)^+$.

Step 2:

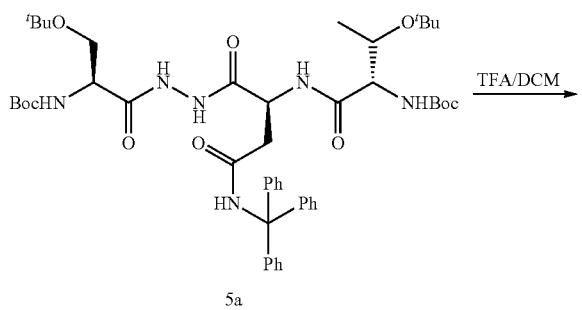

5a

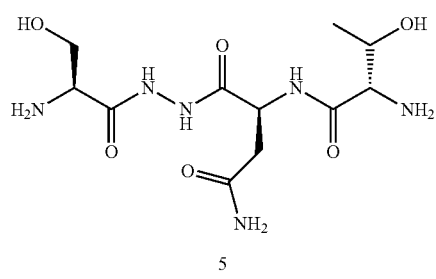

5

To a stirred solution of intermediate 5a (0.47 g) in CH$_2$Cl (5 mL), Trifluoro aceticacid (5 mL) and catalytic amount of tri isopropyl silane were added and stirred for 3 h at room temperature. The resulting solution was concentrated in vacuum to yield 0.15 g of crude compound 5a. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=60% buffer B, 2-20 min=60-5% buffer B with a flow rate of 20 mL/min. HPLC: (method 2): RT –20.8 min.
LCMS: 335.1 (M+H)$^+$.

Example 6

Synthesis of Compound 6

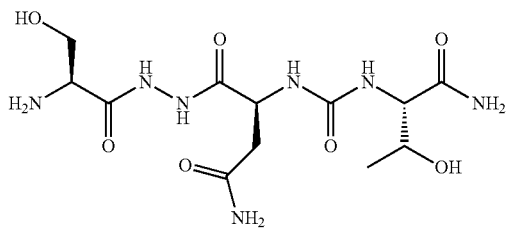 [SMILES: CC(O)[C@H](NC(=O)N[C@@H](CC(N)=O)C(=O)NNC(=O)[C@@H](N)CO)C(N)=O]

DIPEA (0.26 g, 2 mmol) was added slowly to a stirred solution of 2k (0.2 g, 0.33 mmol) and HOBt (0.05 g, 0.4 mmol) in THF (5 mL). The reaction mixture was stirred at room temperature for 5 min. To the above reaction mixture ammonium chloride (0.09 g, 1.7 mmol) was added slowly and stirred at room temperature for 6 h. The completeness of the reaction was confirmed by TLC analysis. The organic layer was washed with 1.0 M Sodium carbonate (50 mL×2), dried over Na$_2$SO$_4$ and evaporated under reduced pressure to yield crude compound 6. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min. The compound was eluted by gradient elution 0-3 min=90% buffer B, 3-20 min=90-40% buffer B with a flow rate of 20 mL/min. HPLC: (method 1) RT –18.2 min.
LCMS: 378.1 (M+H)$^+$.

Example 7

Synthesis of Compound 7

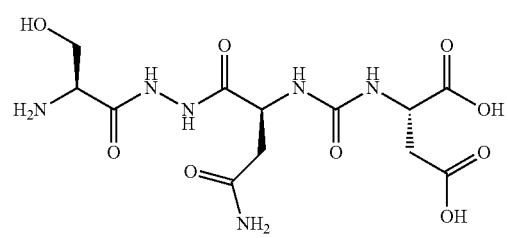 [SMILES: NC(=O)C[C@H](NC(=O)N[C@@H](CC(=O)O)C(=O)O)C(=O)NNC(=O)[C@@H](N)CO]

The compound was synthesised using similar procedure as for compound 2j in (example 2, method B) using H-Asp(O$^t$Bu)-O$^t$Bu instead of H-Thr($^t$Bu)-OBzl The acid labile protecting group was removed as exemplified in (step 5b, method B, example 2) to yield 0.21 g crude material of the title compound. LCMS: 393.5 (M+H)$^+$.

Example 8

Synthesis of Compound 8

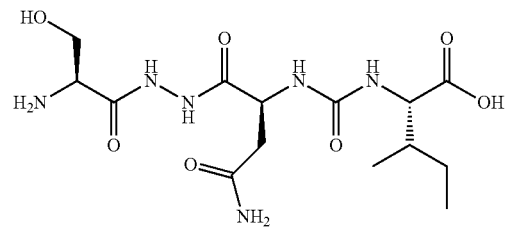 [SMILES: CCC(C)[C@H](NC(=O)N[C@@H](CC(N)=O)C(=O)NNC(=O)[C@@H](N)CO)C(=O)O]

The compound was synthesised using similar procedure as for compound 2k in (example 2, method B) using H-Ile-OBzl instead of H-Thr($^t$Bu)-OBzl. The acid labile protecting group was removed as exemplified in (step 5b, method B, example 2) to yield 0.18 g crude material of the title compound. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-20 min=90-40% buffer B with a flow rate of 20 mL/min. HPLC: (method 1): RT –12.9 min. LCMS: 391.5 (M+H)$^+$.

Example 9

Synthesis of Compound 9

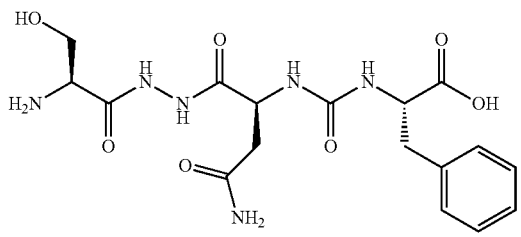 [SMILES: NC(=O)C[C@H](NC(=O)N[C@@H](Cc1ccccc1)C(=O)O)C(=O)NNC(=O)[C@@H](N)CO]

The compound was synthesised using similar procedure as for compound 2k in (example 2, method B) using H-Phe-OBzl instead of H-Thr(ᵗBu)-OBzl. The acid labile protecting group was removed as exemplified in (step 5b, method B, example 2) to yield 0.25 g of the title compound. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-20 min=90-40% buffer B with a flow rate of 20 mL/min. HPLC: (method 1): RT −12.7 min. LCMS: 425.2 (M+H)$^+$.

Example 10

Synthesis of Compound 10

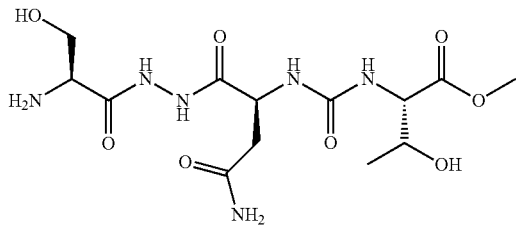 [SMILES: COC(=O)[C@@H](NC(=O)N[C@@H](CC(N)=O)C(=O)NNC(=O)[C@@H](N)CO)C(C)O]

The compound was synthesised using exactly similar procedure as compound 2a (example 2, method A) using H-Thr(ᵗBu)-OMe instead of H-Thr(ᵗBu)-OBzl. Acid labile protecting group was removed using ethyl acetate HCl. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-20 min=90-40% buffer B with a flow rate of 20 mL/min. HPLC: (method 2): RT −14.9 min. LCMS: 393.4 (M+H)$^+$.

Example 11

Synthesis of Compound 11

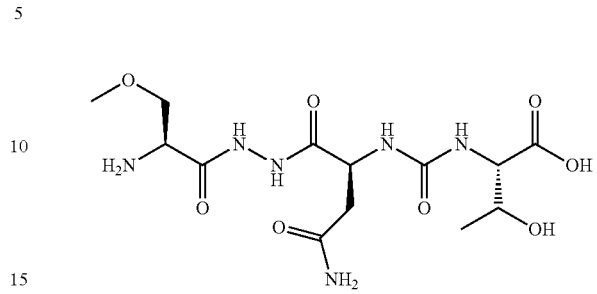

The compound was synthesised using exactly similar procedure as for compound 2k in (example 2, method B) using N-Boc-Ser(OMe)—OH instead of N-Boc-Ser(ᵗBu)-OH. Acid labile protecting group was removed using TFA deprotection as exemplified in (step 3, method A, example 2) to yield 0.1 g crude material of the title compound. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-20 min=90-40% buffer B with a flow rate of 20 mL/min. HPLC: (method 2): RT −13.6 min. LCMS: 393.0 (M+H)$^+$.

Example 12

Synthesis of Compound 12

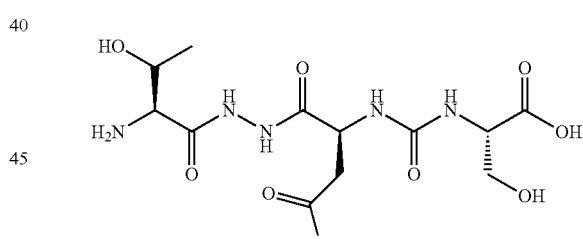

The compound was synthesised using similar procedure as for compound 2j (example 2, method B) and amino acids are linked up in reverse order. Boc-Ser(ᵗBu)-OH was used in place of Boc-Thr(ᵗBu)-OH and H-Ser(ᵗBu)-Oᵗbu was used in place of H-Thr(ᵗBu)-OBzl to yield 0.20 g crude material of the title compound 12. Acid labile protecting group was removed using TFA deprotection as exemplified in (step 5b, method B, example 2) to yield 0.20 g crude material of the title compound. The elution conditions used are Eluent: A: 10 mmol ammonium acetate B: Acetonitrile, Flow rate: 20 mL/min;. The compound was eluted by gradient elution 0-3 min=90% buffer B, 3-20 min=90-50% buffer B with a flow rate of 20 mL/min. HPLC: (method 1): RT −14.4 min. LCMS 379.2 (M+H)$^+$.

Example 13

Synthesis of Compound 13

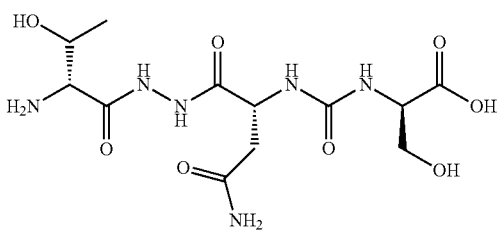 [SMILES: CC(O)[C@@H](N)C(=O)NNC(=O)[C@@H](CC(N)=O)NC(=O)N[C@H](CO)C(=O)O]

The compound was synthesised using similar procedure as for compound 2j (example 2, method B) with D-amino acids linked up in reverse order. Acid labile protecting group was removed using TFA deprotection as exemplified in (step 5b, method B, example 2) to yield 0.12 g crude material of the title compound. The elution conditions used are Eluent: A: 10 mmol ammonium acetate B: Acetonitrile, Flow rate: 20 mL/min;. The compound was eluted by gradient elution 0-3 min=90% buffer B, 3-5 min=90-70% buffer B, 5-40 min=70-40% buffer B with a flow rate of 20 mL/min. HPLC: (method 1): RT −14.7 min. LCMS 379.2 (M+H)$^+$.

Example 14

Synthesis of Compound 14

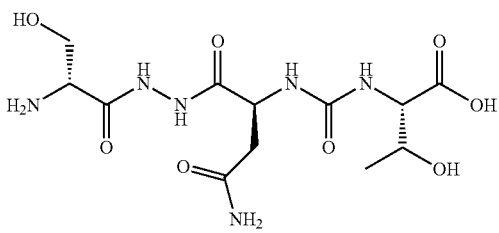 [SMILES: CC(O)[C@H](NC(=O)N[C@@H](CC(N)=O)C(=O)NNC(=O)[C@H](N)CO)C(=O)O]

The compound was synthesised using similar procedure as for compound 2j (example 2, method B). Boc-D-Ser-OH was used in place of Boc-L-Ser($^t$Bu)-OH. Acid labile protecting group was removed using TFA deprotection as exemplified in (step 5b, method B, example 2) to yield 1.5 g crude material of the title compound. The elution conditions used are Eluent: A: 10 mmol ammonium acetate B: Acetonitrile, Flow rate: 20 mL/min;. The compound was eluted by gradient elution 0-3 min=90% buffer B, 3-15 min=90-60% buffer B, 15-19 min=60-5% buffer B with a flow rate of 20 mL/min. HPLC: (method 2): RT −12.3; LCMS: 379.2 (M+H)$^+$.

Example 15

Synthesis of Compound 15

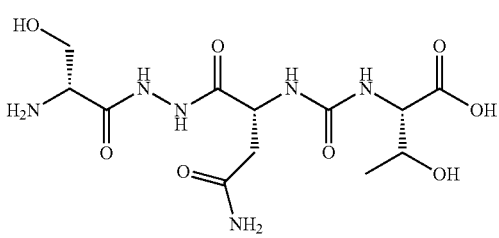 [SMILES: CC(O)[C@H](NC(=O)N[C@H](CC(N)=O)C(=O)NNC(=O)[C@H](N)CO)C(=O)O]

The compound was synthesised using similar procedure as for compound 2j (example 2, method B). Boc-D-Ser($^t$Bu)-OH and Cbz-D-Asn-OH was used in place of Boc-L-Ser($^t$Bu)-OH and Cbz-L-Asn-OH. Acid labile protecting group was removed using TFA deprotection as exemplified in (step 5b, method B, example 2) to yield 0.2 g crude material of the title compound. LCMS: 379.2 (M+H)$^+$.

Example 16

Synthesis of Compound 16

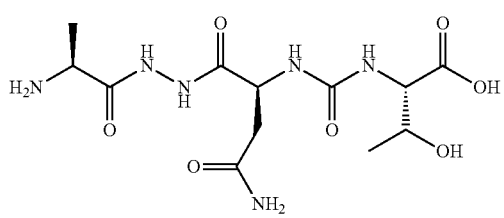 [SMILES: CC(O)[C@H](NC(=O)N[C@@H](CC(N)=O)C(=O)NNC(=O)[C@H](C)N)C(=O)O]

The compound was synthesised using similar procedure as for compound 2j (example 2, method B). Boc-Ala-OH was used in place of Boc-Ser($^t$Bu)-OH. Acid labile protecting group was removed using TFA deprotection as exemplified in (step 5b, method B, example 2) to yield 0.35 g crude material of the title compound. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-16 min=90-40% buffer B with a flow rate of 20 mL/min. HPLC: (method 1): RT −15.8; LCMS: 345.1 (M+H)$^+$.

Example 17

Synthesis of Compound 17

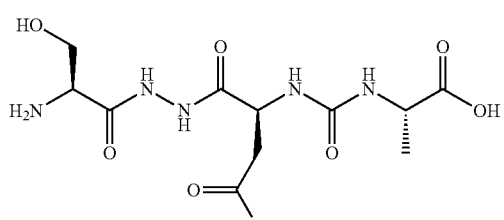

The compound was synthesised using similar procedure as for compound 2j (example 2, method B). H-Ala-O$^t$Bu used in place of H-Thr($^t$Bu)-OBzl. Acid labile protecting group was removed using TFA deprotection as exemplified in (step 5b, method B, example 2) to yield 0.2 g crude material of the title compound. LCMS: 349.3 (M+H)$^+$.

Example 18

Synthesis of Compound 18

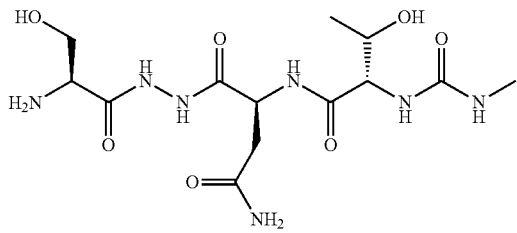 [SMILES: CNC(=O)N[C@H](C(=O)N[C@@H](CC(N)=O)C(=O)NNC(=O)[C@@H](N)CO)C(C)O]

The compound was synthesised using similar procedure as for compound 2i (example 2, method B). Amide bond formation and further reaction was carried out to compound 2i using intermediate 18c instead of N-Boc-Thr(O$^t$Bu)-OH as detailed in example 5 to yield 0.45 g crude material of the title compound. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-20 min=90-40% buffer B with a flow rate of 20 mL/min. HPLC: (method 1): RT –15.8, LCMS: 391.9 (M+H)$^+$.

Synthesis of Compound 18c

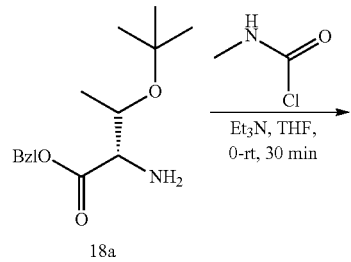

18a

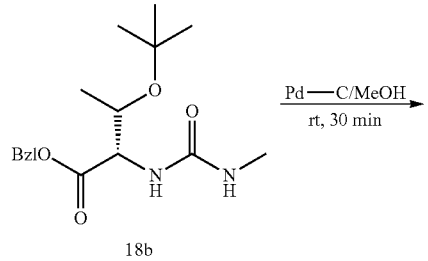

18b

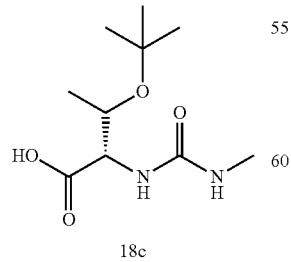

18c

The compound (18c) was synthesised using procedure as mentioned in step 1 of example 2. The urea linkage was carried out using coupling of compound 18a (2.5 g, 9.42 mmol) in THF (25 mL) at room temperature, with N-methylcarbornylchloride (1.05 g, 11.3 mmol). The coupling was initiated by the addition of TEA (1.42 g, 14.13 mmol) and the resultant mixture was stirred at room temperature. After the completion of 30 min, THF was evaporated from the reaction mass, and partitioned between water and ethylacetate. Organic layer was washed with water, brine, dried over Na$_2$SO$_4$ and evaporated under reduced pressure to yield 18b, which was further purified by silica gel column chromatography (Eluent: 0-50% ethyl acetate in Hexane) to yield 2.2 g of product 18b (Yield: 73.3%); LCMS: 323.3 (M+H)$^+$, 345.5 (M+Na)$^+$.

To a solution of compound 18b (2.2 g) in methanol (20 mL) under inert atmosphere, was added 10% Pd—C (0.5 g) and the mixture was stirred for 1 h under H$_2$ atmosphere. The completion of the reaction was confirmed by TLC analysis. The Pd—C catalyst was then removed by filtration through a celite pad, which was then washed with 20 mL of methanol. The combined organic filtrate on evaporation under reduced pressure resulted in the isolation of the compound 18c in quantitative yield. LCMS: 233.2 (M+H)$^+$.

Example 19

Synthesis of Compound 19

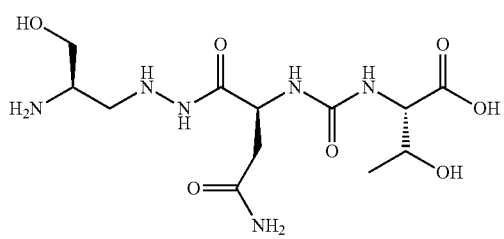 [SMILES: CC(O)[C@H](NC(=O)N[C@@H](CC(N)=O)C(=O)NNC[C@@H](N)CO)C(=O)O]

The compound is similar to Example-2 compound 2 but carbonyl corresponding to Serine is reduced:

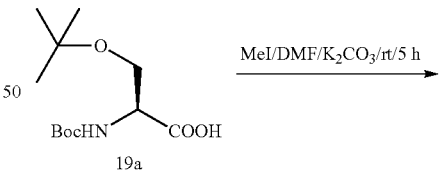

19a

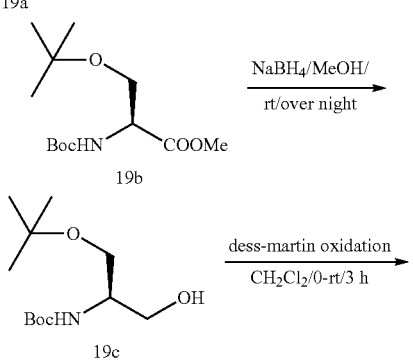

19b

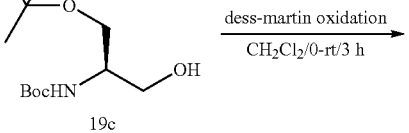

19c

Step 2:

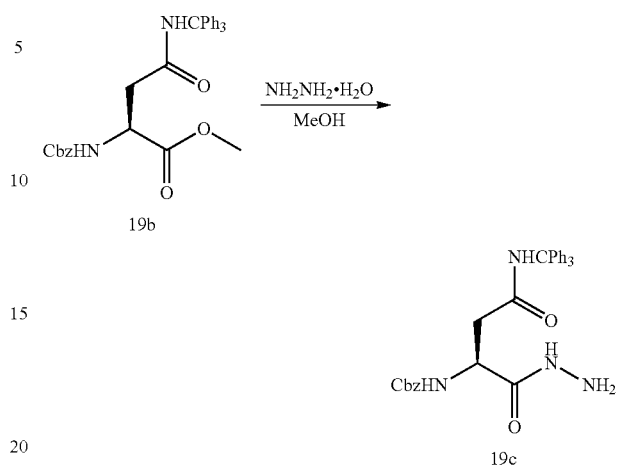

Hydrazine hydrate (2.58 g, 51.72 mmol) was added to the solution of compound 19b (3 g, 5.7 mmol) in methanol (75 mL) and stirred at room temperature for 6 h. The completeness of the reaction was confirmed by TLC analysis. The reaction mixture was evaporated under reduced pressure to yield 2.9 g of pure compound 19c.

LCMS: 523.5 $(M+H)^+$.

Step 3:

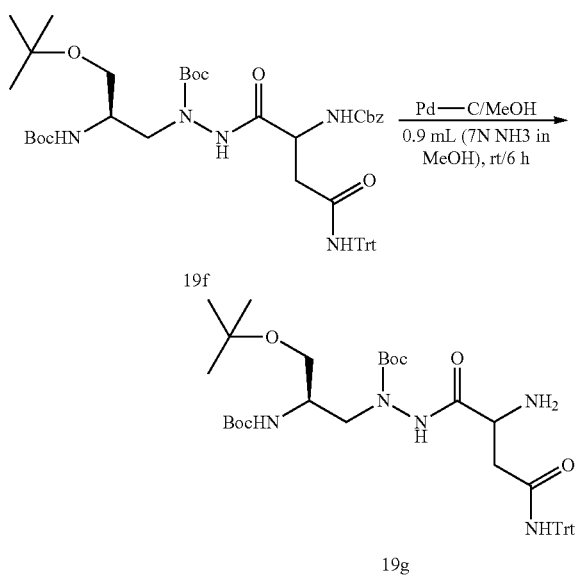

Comp-19c (7.7 g, 14.7 mmol) and Comp-19k (3.0 g, 12.2 mmol) were mixed in THF:MeOH (75:75 mL) at 0° C. and then allowed to stir at rt for 15 min. Again reaction mixture was cooled to 0° C. and treated with Acetic acid (1.87 g, 30.6 mmol) and sodium borohydride (3.8 g, 61.2 mmol) and then mixture was allowed to stir at rt under $N_2$ atmosphere for 12 h until the reactants were consumed as determined by TLC analysis. The reaction mixture was quenched by adding water and the product was extracted with ethyl acetate. The organic extract was washed with 5% $NaHCO_3$ solution (50 mL×2) 5% citric acid solution (50 mL×2), brine (50 mL) and dried $(Na_2SO_4)$. The solvent was evaporated to give the crude product which was further purified by diethyl ether wash to yield 4.4 g pure compound 19d. LCMS: 752.9 $(M+H)^+$.

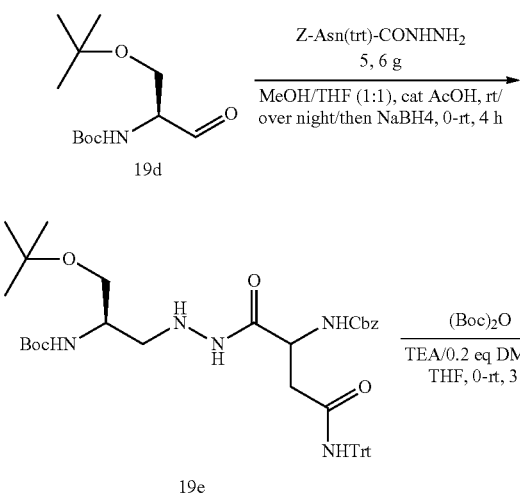

Step 1:

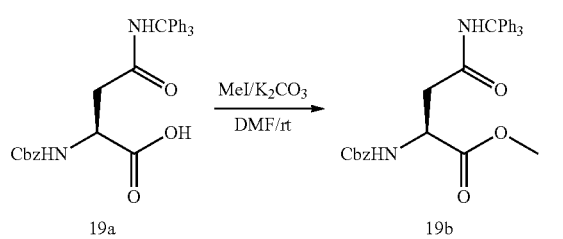

A suspension of $K_2CO_3$ (4.9 g, 35.4 mmol) and Compound 19a (12 g, 23.6 mmol) in DMF (75 mL) at 0° C. was stirred at room temperature for 5 min. To the above suspension MeI (4.05 g, 28.3 mmol) was added and stirred at rt for 5 h. The completeness of the reaction was confirmed by TLC analysis. The reaction mixture was concentrated under reduced pressure to yield 10 g pure compound 19b.

LCMS: 523.4 $(M+H)^+$.

Step 4:

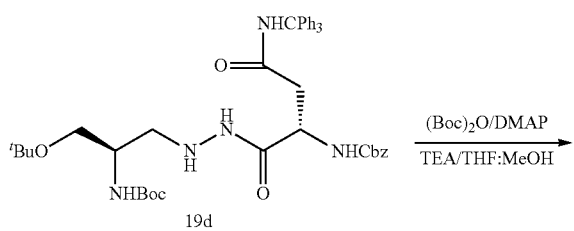

Compound 19d (1.5 g, 1.99 mmol) was dissolved in 75 mL of THF containing triethyl amine (0.6 g, 6.0 mmol) and DMAP (catalyst) at 0° C. At same temperature Boc-anhydride (1.3 g, 6.0 mmol) was added slowly, and stirred for 5 min then allowed to stirr at rt for 4 h under $N_2$ atmosphere until the reactants were consumed as determined by TLC analysis. The reaction mixture was quenched by adding water, and the product was extracted with ethyl acetate. The organic extract was washed with water (50 mL×2), brine (50 mL) and dried ($Na_2SO_4$). The solvent was evaporated to yield 1.5 g compound 19e. LCMS: 852.6 $(M+H)^+$.

Step 5:

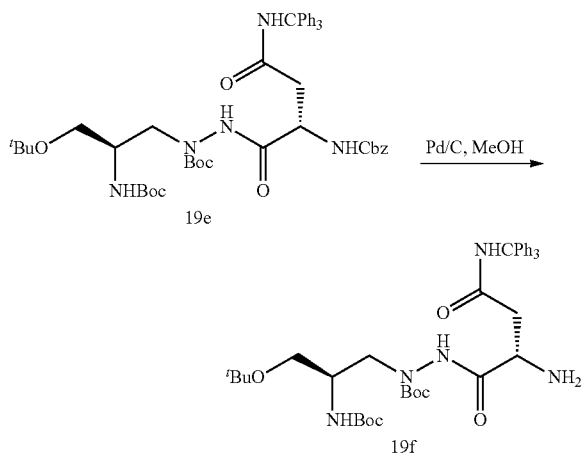

To a solution of compound 19e (1.6 g) in 0.7 N methanolic ammonia (15.0 mL) under inert atmosphere, was added 10% Pd—C (0.3 g) and the mixture was stirred for 1 h under $H_2$ atmosphere. The completion of the reaction was confirmed by TLC analysis. The Pd—C catalyst was then removed by filtration through a celite pad, which was then washed with 20 mL of methanol. The combined organic filtrate on evaporation under reduced pressure resulted in the isolation of 1 g compound 19f in quantitative yield.

LCMS: 718.6 $(M+H)^+$.

Step 6:

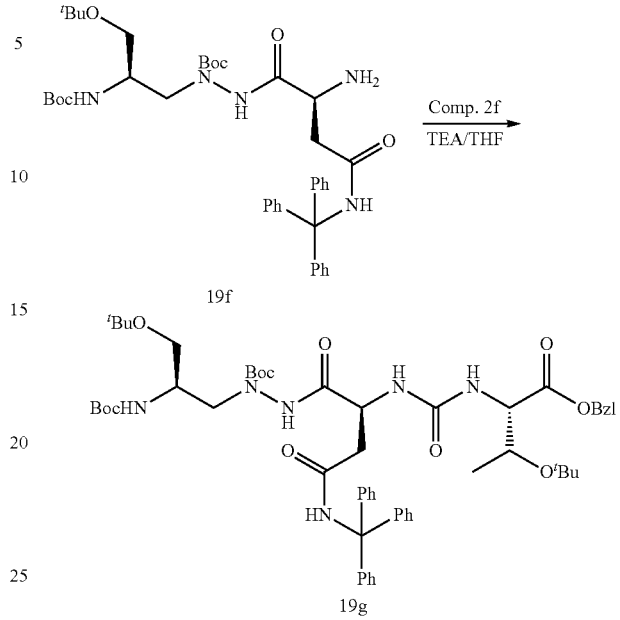

Comp-19f (1.0 g, 1.4 mmol) and Comp-2f (0.72 g, 1.7 mmol) were mixed in THF (20 mL) at room temperature. The coupling was initiated by the addition of TEA (0.21 g, 2.1 mmol) and the resultant mixture was stirred at room temperature. After the completion of 16 h, THF was evaporated from the reaction mass, and partitioned between water and ethyl acetate. Organic layer was washed with water, brine, dried over $Na_2SO_4$ and evaporated under reduced pressure to yield 19 g, which was further purified by diethyl ether wash to yield 1.0 g of compound 19 g in quantitative yield.

LCMS: 1009.8 $(M+H)^+$.

Step 7:

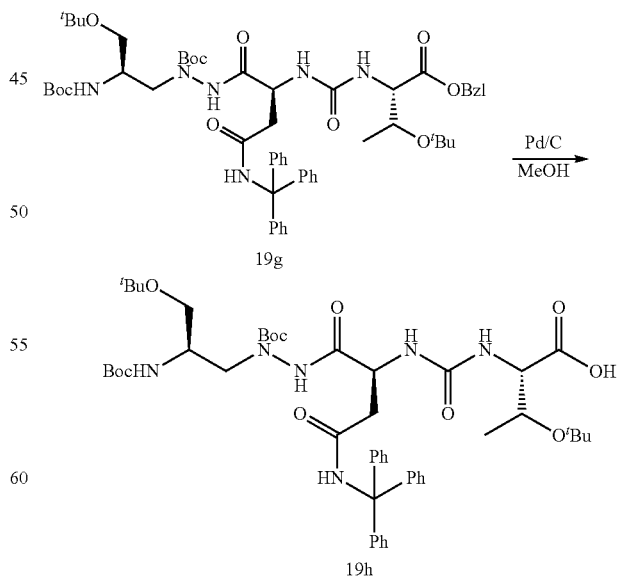

To a solution of compound 19 g (1.0 g) in methanol (20.0 mL) under inert atmosphere, was added 10% Pd—C (0.25 g)

and the mixture was stirred for 1 h under H₂ atmosphere. The completion of the reaction was confirmed by TLC analysis. The Pd—C catalyst was then removed by filtration through a celite pad, which was then washed with 20 mL of methanol. The combined organic filtrate on evaporation under reduced pressure resulted in the isolation of 0.8 g of compound 19 h in quantitative yield. LCMS: 920.2 (M+H)⁺.

Step 8:

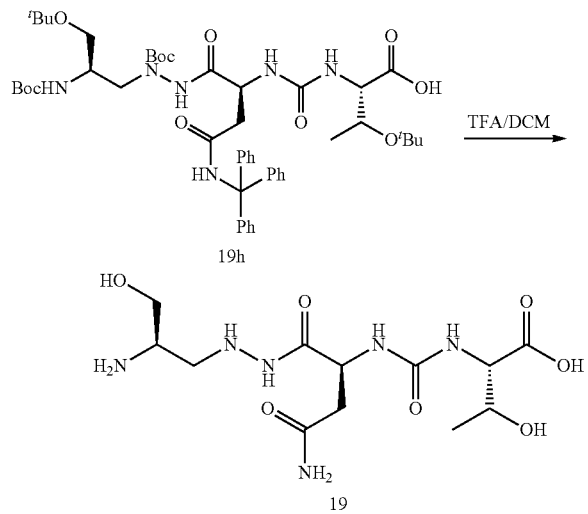

To a solution of compound 19 h (0.8 g) in CH₂Cl₂ (10 mL), Trifluoro aceticacid (5 mL) and catalytic amount of tri isopropyl silane were added and stirred for 3 h at room temperature. The resulting solution was concentrated in vacuum to yield 0.25 g of compound 19 the crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-3 min=90% buffer B, 3-20 min=90-40% buffer B with a flow rate of 20 mL/min. HPLC: (method 1): RT −17.7; LCMS: 365.3 (M+H)⁺.

Synthesis of Boc-Ser(ᵗBu)-Aldehyde, compound 19j

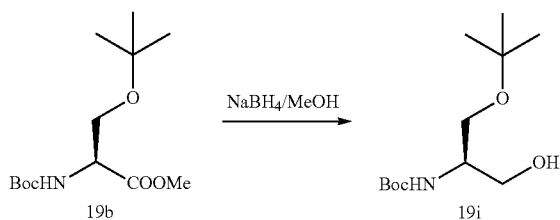 [SMILES: COC(=O)[C@H](COC(C)(C)C)NC(=O)OC(C)(C)C ; CC(C)(C)OC[C@@H](CO)NC(=O)OC(C)(C)C]

To a solution of compound 19b (25 g, 90.8 mmol) in MeOH (200 mL) at 0° C., was added NaBH₄ (17.2 g, 454.2 mmol and stirred at room temperature for 5 h. MeOH was evaporated from the reaction mass, and partitioned between water and ethyl acetate. Organic layer was washed with water, brine, dried over Na₂SO₄ and evaporated under reduced pressure to yield 20 g of 19i in quantitative yield. LCMS: 248.2 (M+H)⁺.

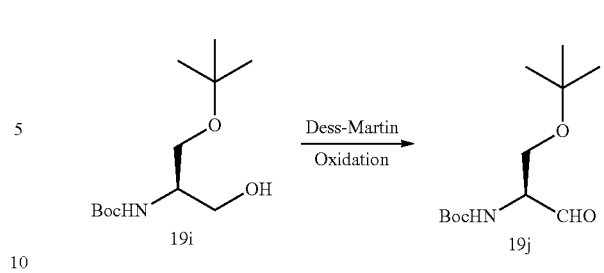

To the solution of N-Boc-aminol 19i (22 g, 89.1 mmol) in CH₂Cl₂ (200 mL) Dess-Martin reagent (41.6 g, 98 mmol) was added portion wise at 0° C. and stirred at room temperature under N₂ atmosphere for 30 min until the reactants were consumed as determined by TLC analysis. The reaction mixture was quenched by adding 1M Na₂S₂O₃ solution, and the product was extracted with CH₂Cl₂. The organic extract was washed with 5% NaHCO₃ solution (20 mL×2), brine (20 mL) and dried (Na₂SO₄). The solvent was evaporated to give the crude product which was further purified by silica gel column chromatography to yield 16 g pure compound 19j (Boc-Ser (ᵗBu)-Aldehyde.

LCMS: 247.9 (M+H)⁺.

Example 20

Synthesis of Compound 20

Step 1:

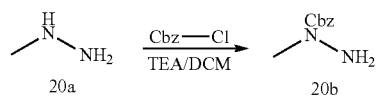

Compound 20a (5 g, 108.7 mmol) was dissolved in 15-20 mL of CH₂Cl₂ containing triethyl amine (13.2 g, 130.4 mmol) at −78° C. At same temperature Cbz-Cl (14.8 g, 86.9 mmol) was added slowly, and stirred for 15 min then allowed to stirr at room temperature for 4 h under N₂ atmosphere until the reactants were consumed as determined by TLC analysis. The reaction mixture quenched by adding water, and the product was extracted with ethyl acetate. The organic extract was washed with water (50 mL×2), brine (50 mL) and dried (Na₂SO₄). The solvent was evaporated to give and purified by column chromatography (25% EtOAc in Hexane) 8 g pure compound 20b. LCMS: 180.09 (M+H)⁺.

Step 2:

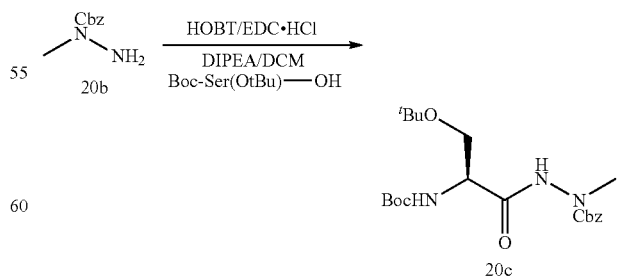

Compound 20b (5 g, 27.7 mmol) and Boc-Ser (OᵗBu)-OH (7.2 g, 27.7 mmol.), HOBt (4.5 g, 33.2 mmol.) and EDC.HCl (6.3 g, 33.2 mmol) were mixed in THF (75 mL), finally was added DIPEA (8.9 g, 69.2 mmol) and stirred at room temperature for 12 h. The completeness of the reaction was confirmed by TLC analysis. THF was evaporated from reaction mixture was then partitioned between ice water and EtOAc. Organic layer layer was washed with 10% NaHCO$_3$, Citric acid, brine solution, dried over Na$_2$SO$_4$ and evaporated under reduced pressure to get crude compound which was washed with pentane to yield 8 g of compound 20c. LCMS: 423.24 (M+H)$^+$.

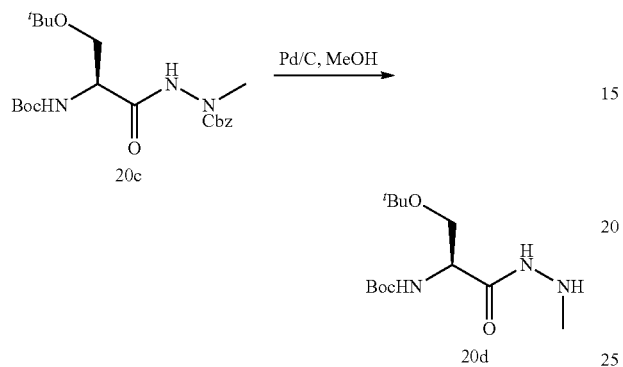

Step 3:

To a solution of compound 20c (8 g) in 0.7 N methanolic ammonia (20.0 mL) under inert atmosphere, was added 10% Pd—C (1.5 g) and the mixture was stirred for 4 h under H$_2$ atmosphere. The completion of the reaction was confirmed by TLC analysis. The Pd—C catalyst was then removed by filtration through a celite pad, which was then washed with 20 mL of methanol. The combined organic filtrate on evaporation under reduced pressure and washed with pentane resulted in the isolation of 4.5 g of compound 20d. LCMS: 190.1 (M-Boc+H)$^+$.

Step 4:

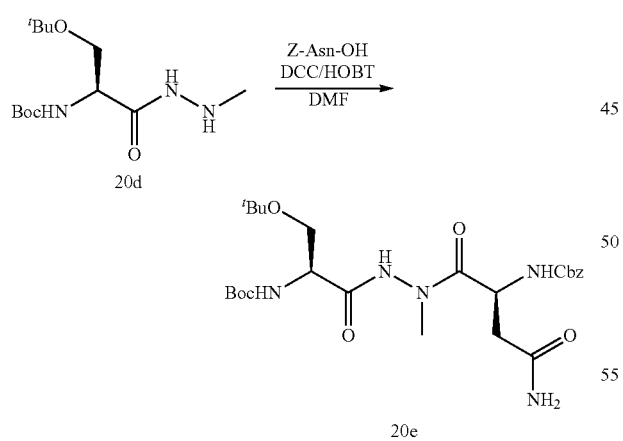

Compound 20d (4.5 g, 15.6 mmol) and Z-Asn-OH (4.2 g, 15.6 mmol), HOBt (4.2 g, 31.2 mmol) and DCC (8 g, 39.0 mmol) were mixed in DMF (50 mL), and stirred at room temperature for 48 h. The completeness of the reaction was confirmed by TLC analysis. The reaction mixture was then partitioned between ice water and ethyl acetate. The organic layer was washed with 10% NaHCO$_3$, Citric acid, brine solution, dried over Na$_2$SO$_4$ and evaporated under reduced pressure and purified by column chromatography (60-120 mesh, 2% MeOH in CH$_2$Cl$_2$) to yield 1.8 g of pure compound 20e.
LCMS: 538.7 (M+H)$^+$.

Step 5:

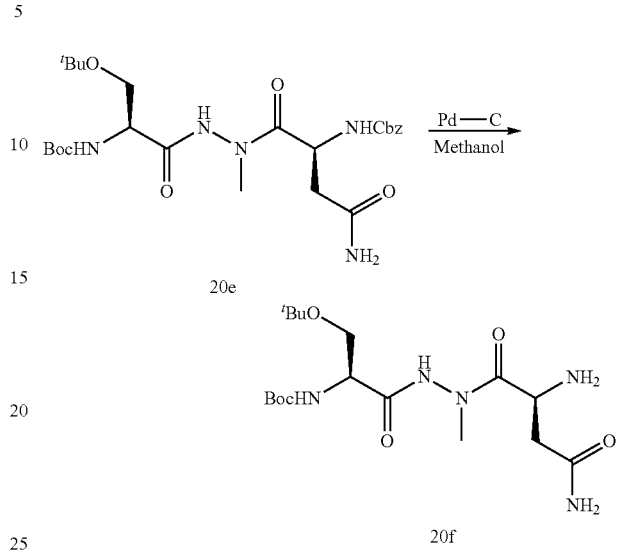

To a solution of compound 20e (1.8 g) in 0.7 N methanolic ammonia (17.5 mL) under inert atmosphere, was added 10% Pd—C (1.8 g) and the mixture was stirred for 1 h under H$_2$ atmosphere. The completion of the reaction was confirmed by TLC analysis. The Pd—C catalyst was then removed by filtration through a celite pad, which was then washed with 20 mL of methanol. The combined organic filtrate on evaporation under reduced pressure to yield crude compound which was washed with pentane resulted in the isolation of 0.9 g of compound 20f.
LCMS: 404.6 (M+H)$^+$.

Step 6:

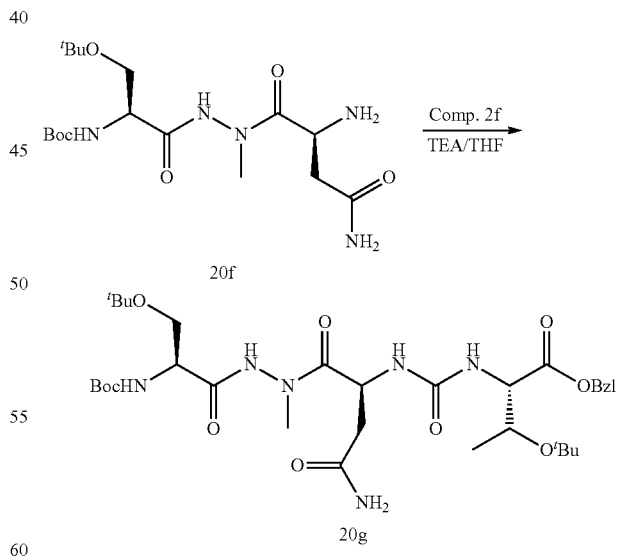

Compound 20f (0.9 g, 2.23 mmol) and Compound 2f (0.95 g, 2.23 mmol) were mixed in THF (20 mL) at room temperature. The coupling was initiated by the addition of TEA (0.33 g, 3.34 mmol) and the resultant mixture was stirred at room temperature. After the completion of 16 h, THF was evaporated from the reaction mass, and partitioned between water and ethyl acetate. Organic layer was washed with water, brine, dried over Na$_2$SO$_4$ and evaporated under reduced pressure to yield compound 20 g, which was further purified by diethyl ether wash to yield 1.4 g of compound 20 g.

LCMS: 695.5 (M+H)$^+$.

Step 7:

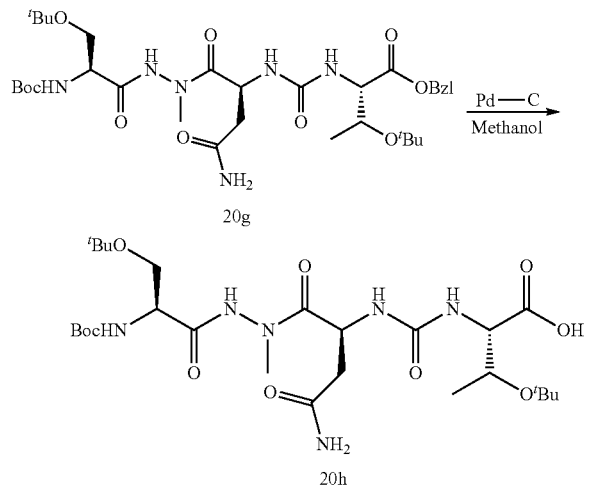

20g

20h

To a solution of compound 20 g (1.4 g) in methanol (10.0 mL) under inert atmosphere, was added 10% Pd—C (0.3 g) and the mixture was stirred for 1 h under H$_2$ atmosphere. The completion of the reaction was confirmed by TLC analysis. The Pd—C catalyst was then removed by filtration through a celite pad, which was then washed with 20 mL of methanol. The combined organic filtrate on evaporation under reduced pressure resulted in the isolation of the compound 20 h in quantitative yield. LCMS: 605.7 (M+H)$^+$.

Step 7:

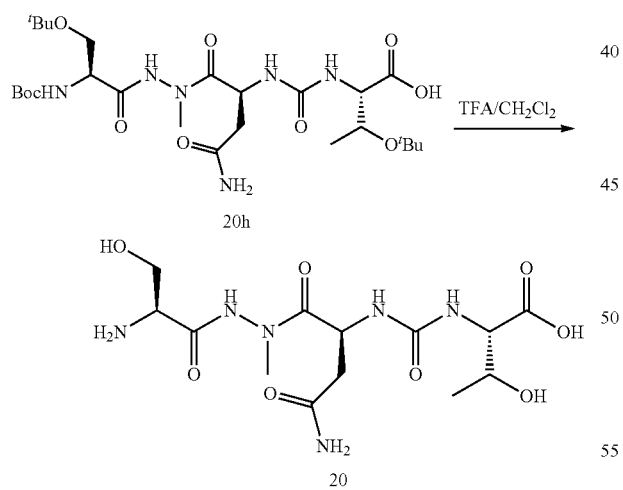

20h

20

To a solution of compound 20 h (1.3 g) in CH$_2$Cl$_2$ (10 mL), Trifluoro aceticacid (5 mL) and catalytic amount of tri isopropyl silane were added and stirred for 3 h at room temperature. The resulting solution was concentrated in vacuum and the solid crude compound 20 (0.7 g) was purified by preparative HPLC method. ZIC HILIC 200A column (21.2 mm×150 mm, 5 µm). The elution conditions used are Eluent: A: 10 mmol ammonium acetate B: Acetonitrile, Flow rate: 20 mL/min;. The compound was eluted by gradient elution 0-3 min=90% buffer B, 3-20 min=90-67% buffer B with a flow rate of 20 mL/min. HPLC: (method 1): RT –14.6; LCMS: 393.4 (M+H)$^+$.

Example 21

Synthesis of Compound 21

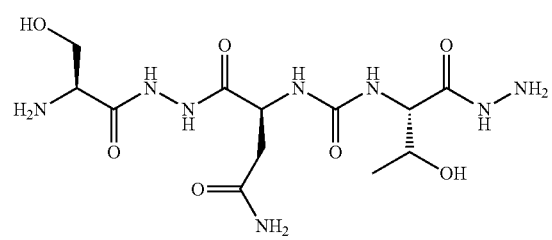 [SMILES: CC(O)[C@H](NC(=O)N[C@@H](CC(N)=O)C(=O)NNC(=O)[C@@H](N)CO)C(=O)NN]

The compound was synthesised using exactly similar procedure as compound 2j (example 2, method B) using H-Thr($^t$Bu)-OMe instead of H-Thr($^t$Bu)-OBzl. The resulting compound (1 g, 1.65 mmol) was treated with Hydrazine hydrate (5 mL) in methanol (20 mL) and stirred at room temperature for 12 h. The completeness of the reaction was confirmed by TLC analysis. The reaction mixture was evaporated under reduced pressure to yield 0.7 g of crude compound 21. The crude material was purified by preparative HPLC using ZIC HILIC 200A column (21.2 mm×150 mm, 5 µm). The elution conditions used are Eluent: A: 10 mmol ammonium acetate B: Acetonitrile, Flow rate: 20 mL/min. The compound was eluted by gradient elution 0-3 min=90% buffer B, 3-20 min=90-40% buffer B with a flow rate of 20 mL/min. HPLC: (method 1) RT –14.1 min. LCMS: 393.2 (M+H)$^+$.

Example 22

Synthesis of Compound 22

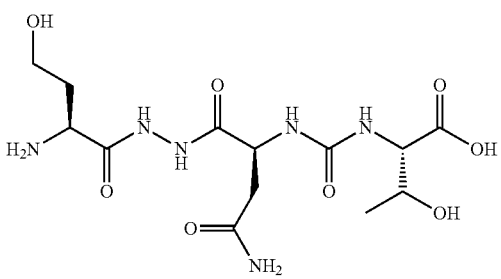 [SMILES: CC(O)[C@H](NC(=O)N[C@@H](CC(N)=O)C(=O)NNC(=O)[C@@H](N)CCO)C(=O)O]

The compound was synthesised using exactly similar procedure as for compound 2j in (example 2, method B) using N-Boc-homoSer(OBzl)-OH instead of N-Boc-Ser($^t$Bu)-OH. Debenzylation and acid labile protecting group was removed as exemplified in (step 4b & 5b, method B, example 2) to yield 0.6 g crude material of the title compound 22. The crude material was purified by preparative HPLC using ZIC HILIC 200A column (21.2 mm×150 mm, 5 µm). The elution conditions used are Eluent: A: 10 mmol ammonium acetate B: Acetonitrile, Flow rate: 20 mL/min;. The compound was eluted by gradient elution 0-3 min=90% buffer B, 3-20 min=90-60% buffer B with a flow rate of 20 mL/min. HPLC: (method 1): RT –15.8 min. LCMS: 393.1 (M+H)$^+$.

Example 23

Synthesis of Compound 23

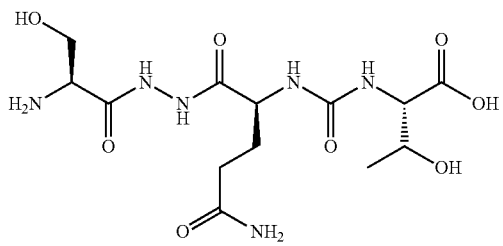 [SMILES: CC(O)[C@H](NC(=O)N[C@@H](CCC(N)=O)C(=O)NNC(=O)[C@@H](N)CO)C(=O)O]

The compound was synthesised using exactly similar procedure as for compound 2 in (example 2, method A) using N-Cbz-Gln (Trt)-OH instead of Z-Asn(Trt)-OH to yield 0.6 g crude material of the title compound 23. LCMS: 393.4 (M+H)⁺.

Example 24

Synthesis of Compound 24

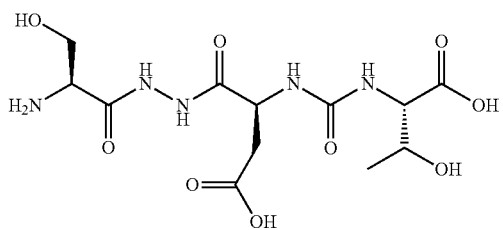 [SMILES: CC(O)[C@H](NC(=O)N[C@@H](CC(=O)O)C(=O)NNC(=O)[C@@H](N)CO)C(=O)O]

The compound was synthesised using exactly similar procedure as for compound 2 in (example 2, method B) using N-Cbz-Asp (O$^t$Bu)-OH instead of Z-Asn(Trt)-OH to yield 0.15 g crude material of the title compound 24. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-3 min=90% buffer B, 3-20 min=90-40% buffer B with a flow rate of 20 mL/min. HPLC: (method 1): RT −14.5 min. LCMS: 380.3 (M+H)⁺.

Example 25

Synthesis of Compound 25

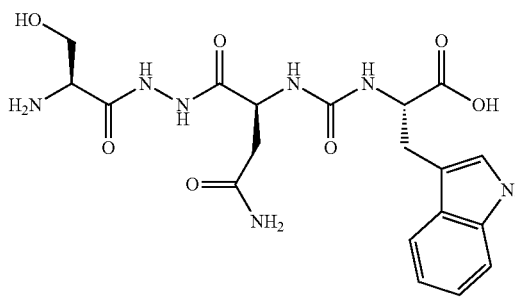

The compound was synthesised using exactly similar procedure as for compound 2 in (example 2, method B) using H-Trp(Boc)-OBzl instead of H-Thr($^t$Bu)-OBzl to yield 0.28 g crude material of the title compound 25. The crude material was purified by preparative HPLC using ZIC HILIC 200A column (21.2 mm×150 mm, 5 μm). The elution conditions used are Eluent: A: 10 mmol ammonium acetate B: Acetonitrile, Flow rate: 20 mL/min;. The compound was eluted by gradient elution 0-2 min=90% buffer B, 2-20 min=90-40% buffer B with a flow rate of 20 mL/min. HPLC: (method 2): RT −11.6 min. LCMS: 464.2 (M+H)⁺.

Although the present application has been illustrated by certain of the preceding examples, it is not to be construed as being limited thereby; but rather, the present application encompasses the generic area as hereinbefore disclosed. Various modifications and embodiments can be made without departing from the spirit and scope thereof. For example, the following compounds which can be prepared by following similar procedure as described above with suitable modification known to the one ordinary skilled in the art are also included in the scope of the present application:

TABLE 2

| Comp. No. | Structure |
|---|---|
| 26. | 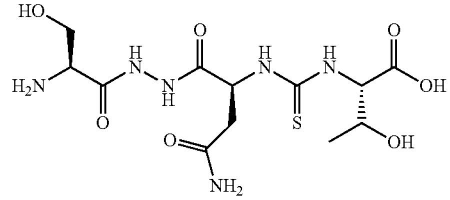 [SMILES: CC(O)[C@H](NC(=S)N[C@@H](CC(N)=O)C(=O)NNC(=O)[C@@H](N)CO)C(=O)O] |
| 27. | 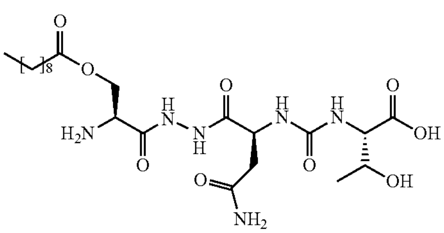 |
| 28. | 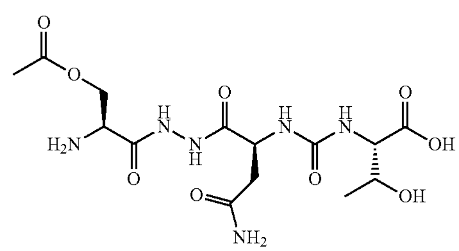 [SMILES: CC(=O)OC[C@H](N)C(=O)NNC(=O)[C@H](CC(N)=O)NC(=O)N[C@H](C(=O)O)C(C)O] |
| 29. | 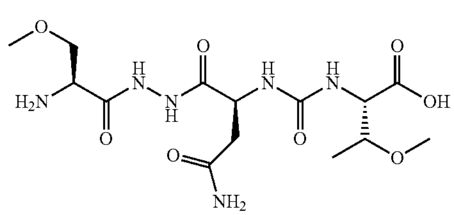 |

TABLE 2-continued

| Comp. No. | Structure |
|---|---|
| 30. | 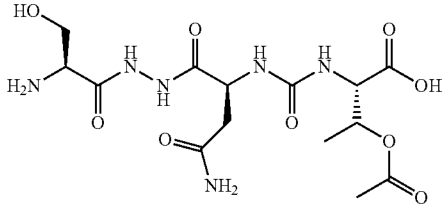 [SMILES: CC(=O)OC(C)[C@H](NC(=O)N[C@@H](CC(N)=O)C(=O)NNC(=O)[C@@H](N)CO)C(=O)O] |
| 31. | 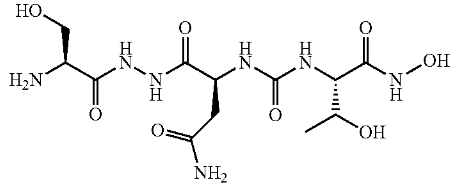 [SMILES: CC(O)[C@H](NC(=O)N[C@@H](CC(N)=O)C(=O)NNC(=O)[C@@H](N)CO)C(=O)NO] |
| 32. | 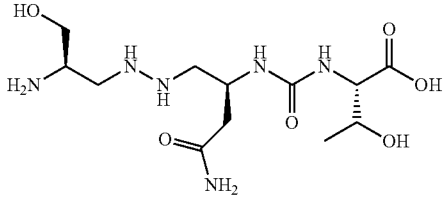 [SMILES: CC(O)[C@H](NC(=O)N[C@H](CNNC[C@@H](N)CO)CC(N)=O)C(=O)O] |
| 33. | 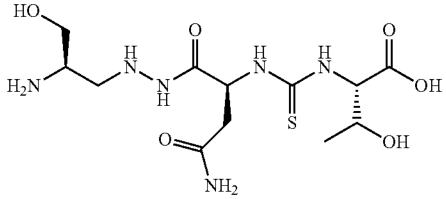 |
| 34. | 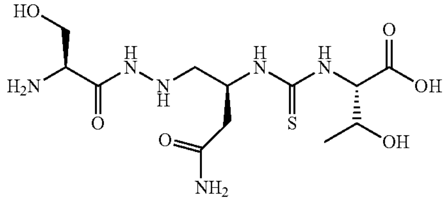 |
| 35. | 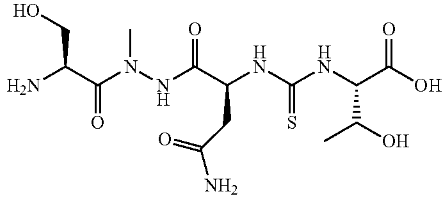 |
| 36. | 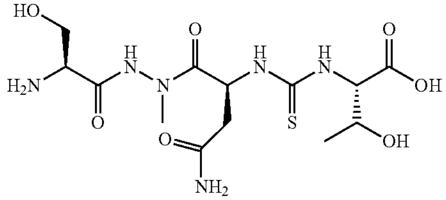 |
| 37. | 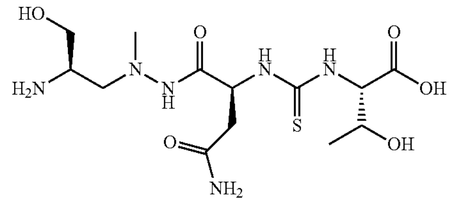 |
| 38. | 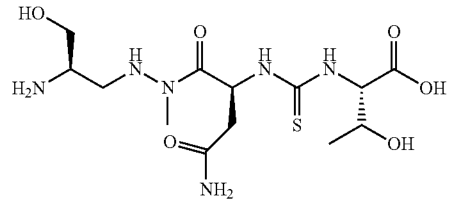 |
| 39. | 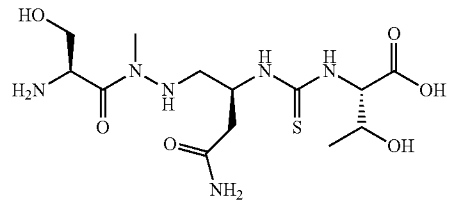 |
| 40. | 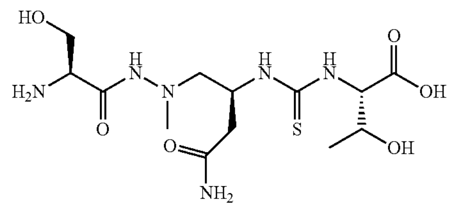 |
| 41. | 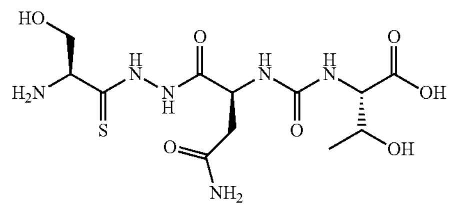 |
| 42. | 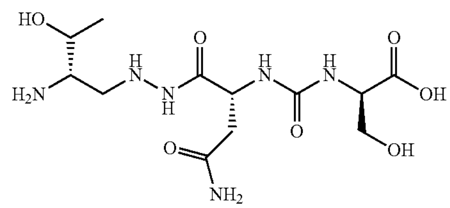 [SMILES: CC(O)[C@@H](N)CNNC(=O)[C@@H](CC(N)=O)NC(=O)N[C@H](CO)C(=O)O] |
| 43. | 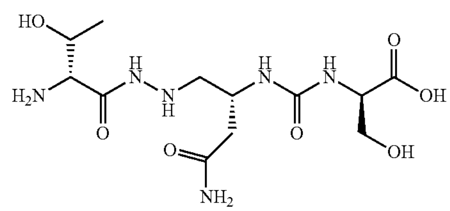 [SMILES: CC(O)[C@@H](N)C(=O)NNC[C@@H](CC(N)=O)NC(=O)N[C@H](CO)C(=O)O] |

TABLE 2-continued

| Comp. No. | Structure |
|---|---|
| 44. | (structure) |
| 45. | (structure) |
| 46. | (structure) |
| 47. | (structure) |
| 48. | (structure) |
| 49. | (structure) |
| 50. | (structure) |
| 51. | (structure) |
| 52. | (structure) |
| 53. | (structure) |
| 54. | (structure) |
| 55. | (structure) |
| 56. | (structure) |
| 57. | (structure) |

TABLE 2-continued

| Comp. No. | Structure |
|---|---|
| 58. | (structure) |
| 59. | (structure) |
| 60. | (structure) |
| 61. | (structure) |
| 62. | (structure) |
| 63. | (structure) |
| 64. | (structure) |
| 65. | (structure) |
| 66. | (structure) |
| 67. | (structure) |
| 68. | (structure) |
| 69. | (structure) |
| 70. | (structure) |
| 71. | (structure) |

TABLE 2-continued

| Comp. No. | Structure |
|---|---|
| 72. | (structure) |
| 73. | (structure) |
| 74. | (structure) |
| 75. | (structure) |
| 76. | (structure) |
| 77. | (structure) |
| 78. | (structure) |
| 79. | (structure) |
| 80. | (structure) |
| 81. | (structure) |
| 82. | (structure) |
| 83. | (structure) |
| 84. | (structure) |
| 85. | (structure) |

TABLE 2-continued

| Comp. No. | Structure |
|---|---|
| 86. | (structure) |
| 87. | (structure) |
| 88. | (structure) |
| 89. | (structure) |
| 90. | (structure) |
| 91. | (structure) |
| 92. | (structure) |
| 93. | (structure) |
| 94. | (structure) |
| 95. | (structure) |
| 96. | (structure) |
| 97. | (structure) |
| 98. | (structure) |
| 99. | (structure) |

TABLE 2-continued

| Comp. No. | Structure |
|---|---|
| 100. | 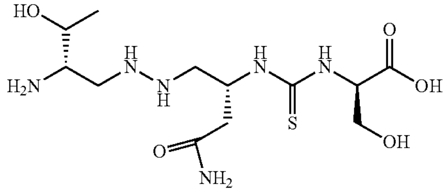 [SMILES: CC(O)[C@@H](N)CNNC[C@@H](CC(N)=O)NC(=S)N[C@H](CO)C(=O)O] |
| 101. | 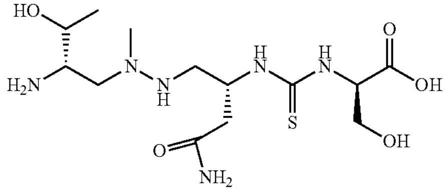 [SMILES: CC(O)[C@@H](N)CN(C)NC[C@@H](CC(N)=O)NC(=S)N[C@H](CO)C(=O)O] |
| 102. | 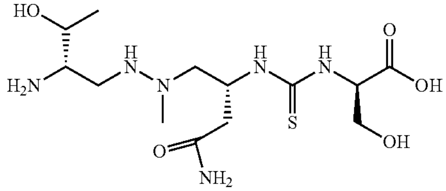 [SMILES: CC(O)[C@@H](N)CNN(C)C[C@@H](CC(N)=O)NC(=S)N[C@H](CO)C(=O)O] |
| 103. | 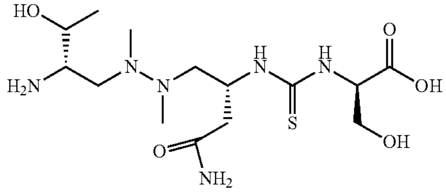 [SMILES: CC(O)[C@@H](N)CN(C)N(C)C[C@@H](CC(N)=O)NC(=S)N[C@H](CO)C(=O)O] |
| 104. | 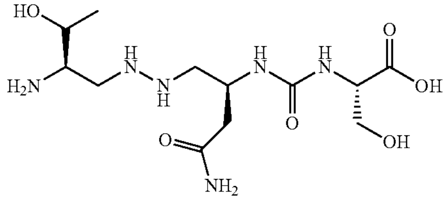 [SMILES: CC(O)[C@H](N)CNNC[C@H](CC(N)=O)NC(=O)N[C@@H](CO)C(=O)O] |
| 105. | 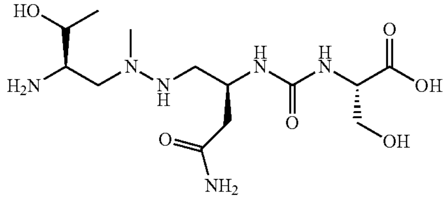 [SMILES: CC(O)[C@H](N)CN(C)NC[C@H](CC(N)=O)NC(=O)N[C@@H](CO)C(=O)O] |
| 106. | 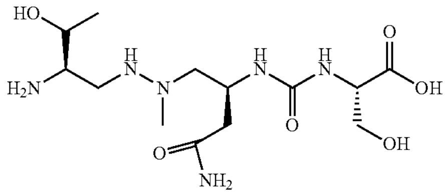 [SMILES: CC(O)[C@H](N)CNN(C)C[C@H](CC(N)=O)NC(=O)N[C@@H](CO)C(=O)O] |
| 107. | 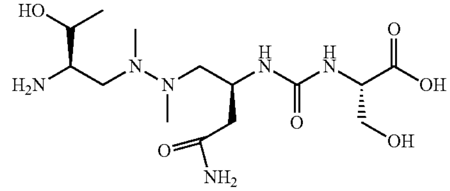 [SMILES: CC(O)[C@H](N)CN(C)N(C)C[C@H](CC(N)=O)NC(=O)N[C@@H](CO)C(=O)O] |
| 108. | 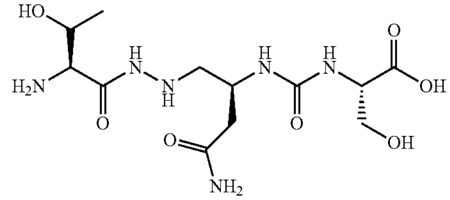 [SMILES: CC(O)[C@H](N)C(=O)NNC[C@H](CC(N)=O)NC(=O)N[C@@H](CO)C(=O)O] |
| 109. | 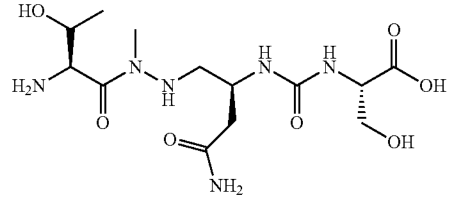 [SMILES: CC(O)[C@H](N)C(=O)N(C)NC[C@H](CC(N)=O)NC(=O)N[C@@H](CO)C(=O)O] |
| 110. | 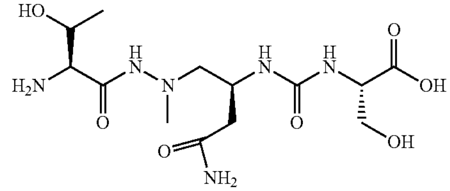 [SMILES: CC(O)[C@H](N)C(=O)NN(C)C[C@H](CC(N)=O)NC(=O)N[C@@H](CO)C(=O)O] |
| 111. | 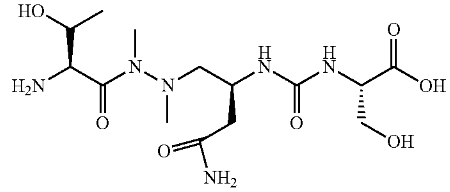 [SMILES: CC(O)[C@H](N)C(=O)N(C)N(C)C[C@H](CC(N)=O)NC(=O)N[C@@H](CO)C(=O)O] |
| 112. | 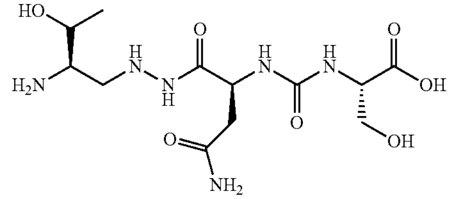 [SMILES: CC(O)[C@H](N)CNNC(=O)[C@H](CC(N)=O)NC(=O)N[C@@H](CO)C(=O)O] |
| 113. | 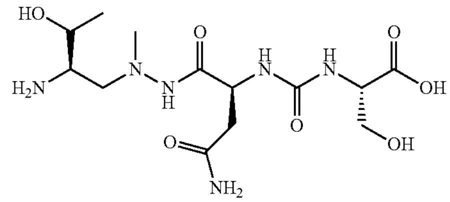 [SMILES: CC(O)[C@H](N)CN(C)NC(=O)[C@H](CC(N)=O)NC(=O)N[C@@H](CO)C(=O)O] |

TABLE 2-continued

| Comp. No. | Structure |
|---|---|
| 114. | (structure) |
| 115. | (structure) |
| 116. | (structure) |

Example 26

The effect of PD1 derived peptidomimetics on mouse splenocyte proliferation inhibited by recombinant PDL1 or tumor cells expressing PDL; analyzed by Fluorescence Activated Cell Shorting (FACS) method using CFSE (Carboxyfluorescein Diacetate Succinimidyl Ester) labeling.

Rescue of Mouse Splenocyte Proliferation in the Presence of Recombinant PD-L1/MDA MB-231 Cells Expressing PDL1:

MDA-MB-231 cells were found to express PD-L1 by RT-PCR and therefore used as a source of PD-L1 in the assays. Alternatively, recombinant human PD-L1 (rh-PDL-1, cat no: 156-B7-100, R&D Systems) was also used as the source of PD-L1.

Requirement:

Mouse splenocytes harvested from 6-8 weeks old C57 BL6 mice; RPMI 1640 (GIBCO, Cat #11875); DMEM with high glucose (GIBCO, Cat # D6429); Fetal Bovine Serum [Hyclone, Cat # SH30071.03]; Penicillin (10000 unit/ml)-Streptomycin (10,000 µg/ml) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (imp (GIBCO, Cat #-A10492); Histopaque (density-1.083 gm/ml) (SIGMA 10831); Trypan blue solution (SIGMA-T8154); 2 ml Norm Ject Luer Lock syringe—(Sigma 2014-12); 40 µm nylon cell strainer (BD FALCON 35230); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 µL of Di methyl Sulfoxide (DMSO $C_2H_6SO$, SIGMA-D-5879) and aliquoted in to tubes for further use. Working concentrations were titrated from 10 µM to 1 µM. (eBioscience—650850-85); 0.05% Trypsin and 0.02% EDTA (SIGMA 59417C); 96-well format ELISA plates (Corning CLS3390); BD FACS caliber (E6016); Recombinant Human B7-H1/PDL1 Fc Chimera (rh-PDL-1, cat no: 156-B7-100);

Protocol

Splenocyte Preparation and Culturing:

Splenocytes harvested in a 50 ml falcon tube by mashing mouse spleen in a 40 µm cell strainer were further treated with 1 ml ACK lysis buffer for 5 mins at room temperature. After washing with 9 ml of RPMI complete media, cells were re-suspended in 3 ml of 1×PBS in a 15 ml tube. 3 ml of Histopaque was added carefully to the bottom of the tube without disturbing overlaying splenocyte suspension. After centrifuging at 800×g for 20 mins at room temperature, the opaque layer of splenocytes was collected carefully without disturbing/mixing the layers. Splenocytes were washed twice with cold 1×PBS followed by total cell counting using Trypan Blue exclusion method and used further for cell based assays.

Splenocytes were cultured in RPMI complete media (RPMI+10% fetal bovine serum+1 mM sodium pyruvate+10,000 units/ml penicillin and 10,000 µg/ml streptomycin) and maintained in a $CO_2$ incubator with 5% $CO_2$ at 37° C.

CFSE Proliferation Assay:

CFSE is a dye that passively diffuses into cells and binds to intracellular proteins. $1\times10^6$ cells/ml of harvested splenocytes were treated with 5 µM of CFSE in pre-warmed 1×PBS/0.1% BSA solution for 10 mins at 37° C. Excess CFSE was quenched using 5 volumes of ice-cold culture media to the cells and incubated on ice for 5 mins. CFSE labelled splenocytes were further given three washes with ice cold complete RPMI media. CFSE labelled $1\times10^5$ splenocytes added to wells containing either MDA-MB231 cells ($1\times10^5$ cells cultured in high glucose DMEM medium) or recombinant human PDL-1 (100 ng/ml) and test compounds. Splenocytes were stimulated with anti-mouse CD3 and anti-mouse CD28 antibody (1 µg/ml each), and the culture was further incubated for 72 hrs at 37° C. with 5% $CO_2$. Cells were harvested and washed thrice with ice cold FACS buffer and % proliferation was analyzed by flow cytometry with 488 nm excitation and 521 nm emission filters.

Data Compilation, Processing and Inference:

Percent splenocyte proliferation was analyzed using cell quest FACS program and fold induction was calculated by normalizing individual values to % background proliferation. Percent rescue of splenocyte proliferation by compound was estimated after deduction of % background proliferation value and normalising to % stimulated splenocyte proliferation (positive control) as 100%.

Background proliferation: Splenocytes+anti-CD3/CD28+PDL or Tumor

Stimulated splenocytes: Splenocytes+anti-CD3/CD28 stimulation

Compound proliferation: Splenocytes+anti-CD3/CD28+PDL or Tumor+Compound

Fold Induction=% splenocyte proliferation/% background proliferation

Compound effect is examined by adding required conc. of compound to anti-CD3/CD28 stimulated splenocytes in presence of ligand (PDL-1) or tumor (Table 2)

$EC_{50}$ was calculated by non-linear regression curve fit using GraphPad Prism 5 software. $EC_{50}$ for compound 2, 12 and 13 were found to be 23 nM, 22 nM and 35 nM respectively in mouse splenocyte proliferation assay inhibited by recombinant human PDL-1 (FIG. 1).

TABLE 3

Rescue of mouse splenocyte proliferation inhibited by MDA-MB-231 tumor cells expressing PD-L1 using CFSE based assay:

| Compound No. | % Splenocyte proliferation | Fold induction |
|---|---|---|
| Background proliferation | 20 | 1.0 |
| Stimulated Splenocytes | 74 | 3.7 |
| 1 | 56 | 2.8 |
| 2 | 68 | 3.4 |
| 4 | 56 | 2.8 |
| 5 | 60 | 3 |
| 6 | 46 | 2.3 |
| 7 | 57 | 2.9 |
| 8 | 60 | 3 |
| 10 | 67 | 3.4 |
| 11 | 44 | 2.2 |
| 13 | 67 | 3.4 |
| 15 | 58 | 2.9 |
| 17 | 59 | 3 |
| 18 | 59 | 3 |

Example 27

Rescue of Splenocyte Effector Function by Monitoring the Release of Interferon (IFN)-γ by ELISA $1\times10^5$ splenocytes (isolated as described earlier) were added to wells containing recombinant mouse PDL-1 (cat no: 1019-B7-100, R&D Systems) or PDL-2 (Cat no: 1022-PL-100, R&D Systems) (both at 100 ng/ml) and test peptidomimetics. Splenocytes were stimulated with anti-mouse CD3 (eBiosciences—16-0032) and anti-mouse CD28 antibody (eBiosciences—16-0281) (1 µg/ml each) and the culture was further incubated for 72 hrs at 37° C. with 5% $CO_2$. After 72 hours of incubation the cell culture supernatants were collected after brief centrifugation of culture plates (200 g×5 mins at 4° C.) and processed for mouse IFN-γ measurement by ELISA following manufacturer's protocol (e Biosciences; 88-7314). In brief, 96 well ELISA plates were coated with 100 µl/well of capture antibody in coating buffer and incubated overnight at 4° C. Plates were washed five times with wash buffer and further blocked with 200 µl of 1× assay diluents for 1 hr at RT. Following wash step, 100 µl of cell culture supernatants were added to wells and further incubated for 2 hrs at RT. Appropriate standards were also included. After wash step, plate was incubated for one hour with 100 µl/well of detection antibody. The wash step was repeated and the plate was incubated for 30 minutes with 100 µl/well of Avidin-HRP. The plate was washed 7 times with wash buffer and incubated for 15 minutes with 100 µl/well of substrate solution. 50 µl of stop solution was added to each well and the plate was read at 450 nm. The absorbance values were then plotted against the standards and the concentration of IFN-γ was determined using GraphPad Prism software. Each experimental condition was carried out in triplicates. Percent IFN-γ release for each test compound concentration was calculated by normalising individual test compound IFN-γ values to anti-CD3+anti-CD28 stimulated IFN-γ value. The percent IFN-γ release by test compounds were calculated using following formula:

% IFN-γ release=[(Test compound IFN-γ−PDL background control)/(anti-CD3+anti-CD28 positive control−PDL background control)]*100.

Test Compound IFN-γ=splenocyte IFN-γ values for the well containing splenocyte+anti-CD3+anti-CD28+PDL1/L2+Test compound.

CD3+CD28 positive control=splenocyte IFN-γ values for the well containing splenocyte+anti-CD3+anti-CD28.

PDL background control=splenocyte IFN-γ values for the well containing splenocyte+anti-CD 3+anti-CD28+PDL1/L2.

TABLE 4

Rescue of splenocyte effector function by monitoring the release of interferon (IFN)-γ by ELISA.

| | $EC_{50}$ (nM) | |
|---|---|---|
| Comp # | In presence of recombinant mouse PDL-1 | In presence of recombinant mouse PDL-2 |
| Comp 2 | 30 nM | 40 nM |
| Comp 12 | 27 nM | 62 nM |
| Comp 13 | 40 nM | 30 nM |

Example 28

In Vivo Efficacy of Compound #2 on Primary Tumour Growth in CT-26 Colon Cancer Model Two million CT26 (murine colon carcinoma) cells injected to male Balb/c mice (s.c) on day 1 and dosing started on Day 5. Each group consisted of ten animals. Tumor volumes were measured 3 times a week, body weight and clinical signs monitored daily. Compound #2 dosed at 3 mg/kg, inhibited the tumour growth to the extent of 46 percent (p<0. p<0.01, 2-way ANOVA) (FIG. 2). There was no body weight reduction and no clinical signs during the period of dosing.

Example 29

In Vivo Efficacy of Compound 2 Against *Pseudomonas aeruginosa* Lung Infection Model Bacterial strain used was ciprofloxacin resistant strain of *P. aeruginosa* AUCC 664. BALB/c mice weighing 18-22 gms were used for the study. Animals were quarantined for a period of 5 days in individually ventilated cages. Food and water was provided ad libitum. Temperature was maintained at 22-26° C. with a light dark cycle of 12 hrs. The inoculum containing $2\times10^8$ CFU/animal was administered to the animals by per oral-intratracheal route. Treatment was initiated after 2 hrs of infection and the compound was administered thrice a day at 10 mg/Kg for 11 days. One group of animals was kept untreated to serve as infection control. Animals were kept under observation for survival up to 15 days (FIG. 3).

What is claimed is:

1. A compound of Formula (I):

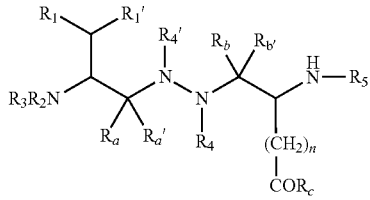

wherein;
$R_1$ is hydrogen, —$OR_6$, —$OC(O)R_6$, halogen, cyano, or hydroxyalkyl;
$R_1'$ is hydrogen or alkyl;
both $R_a$ and $R_a'$ is hydrogen; or together represent an oxo (=O) group or a thioxo (=S) group;
both $R_b$ and $R_b'$ is hydrogen; or together represent an oxo (=O) group or a thioxo (=S) group;
$R_2$ and $R_3$ independently are hydrogen, optionally substituted alkyl or optionally substituted acyl;
$R_4$ and $R_4'$ independently are hydrogen, optionally substituted alkyl or optionally substituted acyl;
$R_6$ is hydrogen or optionally substituted alkyl;
'n' is an integer selected from 1 or 2;
$R_c$ is hydroxyl or amino;
$R_5$ is —C(=X)—$Am_1$—$R_7$;
wherein, X is O or S;
$Am_1$ is an amino acid residue Ser, Asp, Ala, Ile, Phe, Trp, Glu, or Thr; wherein the amino acid residue is optionally substituted with an alkyl or an acyl group;
$R_7$ is an alpha carboxylic group of $Am_1$ which is in free acid, ester or in amide form; wherein the amide nitrogen is optionally substituted with hydroxyl or amino;
or a stereoisomer thereof or a pharmaceutically acceptable salt thereof.

2. The compound according to claim 1, wherein $R_1$ is —OH, —$OCH_3$ or —$OCOCH_3$.

3. The compound according to claim 1, wherein $R_1'$, $R_4$ and $R_4'$ are hydrogen.

4. The compound according to claim 1, wherein $R_5$ is —C(=O)—$Am_1$—$R_7$, wherein $Am_1$ is selected from Ser, Thr, Asp, Trp, Ile or Phe; and $R_7$ is same as defined in claim 1.

5. The compound according to claim 1, wherein the amino acid $Am_1$ is either D or L-amino acid.

6. The compound of claim 1, wherein the compound of Formula (I) is a compound of Formula (IA):

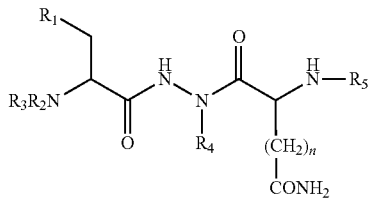

wherein, $R_1$, $R_2$, $R_3$, $R_4$, $R_5$ and 'n' are same as defined in claim 1.

7. The compound of claim 1, wherein the compound of Formula (I) is a compound of Formula (IB):

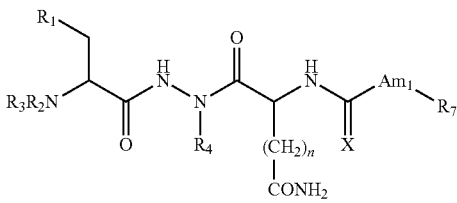

wherein, $R_1$, $R_2$, $R_3$, $R_4$, X, $Am_1$, $R_7$ and 'n' are same as defined in claim 1.

8. The compound of claim 1, wherein the compound of Formula (I) is a compound of Formula (IE):

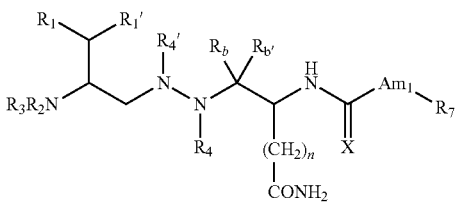

wherein, $R_1$, $R_1'$ $R_2$, $R_3$, $R_4$, $R_4'$, $R_b$, $R_b'$, $R_7$, $Am_1$, X and 'n' are same as defined in claim 1.

9. A compound of a structure that is

| Compound No | Structure |
|---|---|
| 2. | HO... (structure) |
| 3. | HO... (structure) |
| 4. | HO... (structure) |
| 6. | HO... (structure) |

| Compound No | Structure |
|---|---|
| 7. | 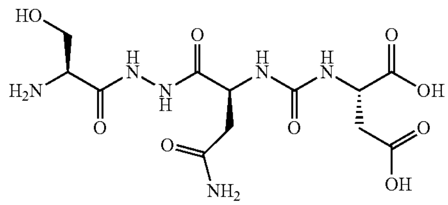 [SMILES: NC(=O)C[C@H](NC(=O)N[C@@H](CC(=O)O)C(=O)O)C(=O)NNC(=O)[C@@H](N)CO] |
| 8. | 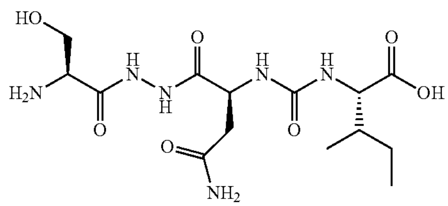 [SMILES: CCC(C)[C@H](NC(=O)N[C@@H](CC(N)=O)C(=O)NNC(=O)[C@@H](N)CO)C(=O)O] |
| 9. | 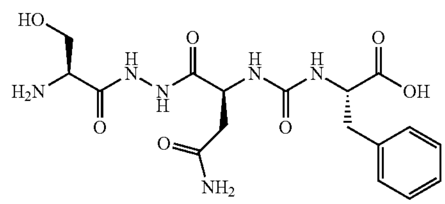 [SMILES: NC(=O)C[C@H](NC(=O)N[C@@H](Cc1ccccc1)C(=O)O)C(=O)NNC(=O)[C@@H](N)CO] |
| 10. | 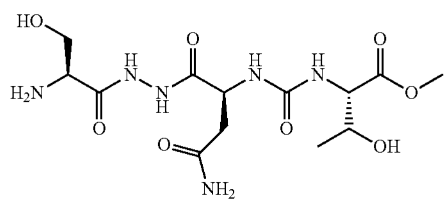 [SMILES: COC(=O)[C@@H](NC(=O)N[C@@H](CC(N)=O)C(=O)NNC(=O)[C@@H](N)CO)C(C)O] |
| 11. | 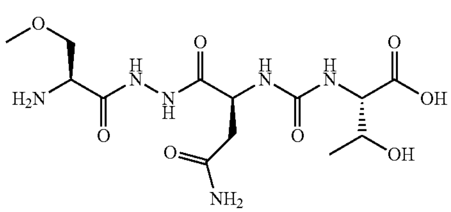 [SMILES: COC[C@H](N)C(=O)NNC(=O)[C@H](CC(N)=O)NC(=O)N[C@H](C(=O)O)C(C)O] |
| 12. | 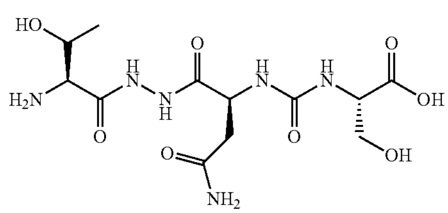 [SMILES: CC(O)[C@H](N)C(=O)NNC(=O)[C@H](CC(N)=O)NC(=O)N[C@@H](CO)C(=O)O] |
| 13. | 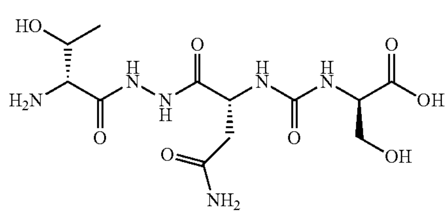 |

| Compound No | Structure |
|---|---|
| 14. | 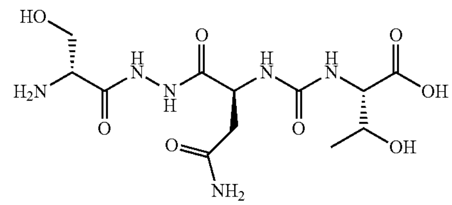 [SMILES: CC(O)[C@H](NC(=O)N[C@@H](CC(N)=O)C(=O)NNC(=O)[C@H](N)CO)C(=O)O] |
| 15. | 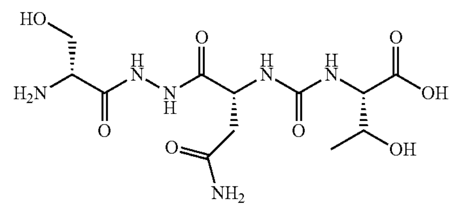 [SMILES: CC(O)[C@H](NC(=O)N[C@H](CC(N)=O)C(=O)NNC(=O)[C@H](N)CO)C(=O)O] |
| 16. | 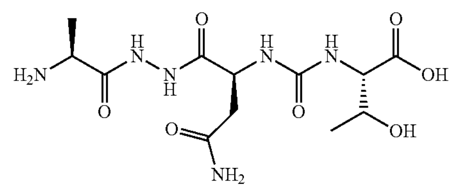 [SMILES: CC(O)[C@H](NC(=O)N[C@@H](CC(N)=O)C(=O)NNC(=O)[C@H](C)N)C(=O)O] |
| 17. | 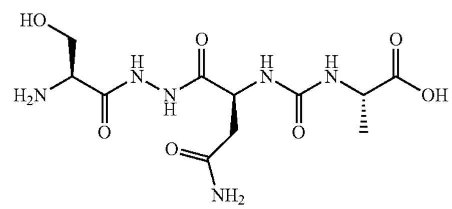 [SMILES: C[C@H](NC(=O)N[C@@H](CC(N)=O)C(=O)NNC(=O)[C@@H](N)CO)C(=O)O] |
| 19. | 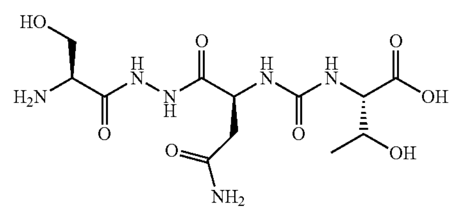 |
| 20. | 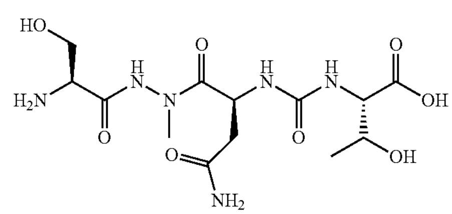 |
| 21. | 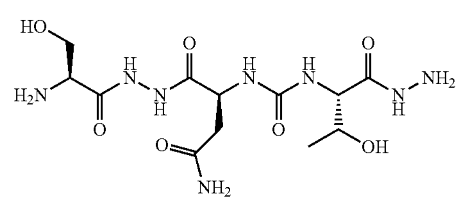 [SMILES: CC(O)[C@H](NC(=O)N[C@@H](CC(N)=O)C(=O)NNC(=O)[C@@H](N)CO)C(=O)NN] |

| Compound No | Structure |
|---|---|
| 22. | (structure) |
| 23. | (structure) |
| 24. | (structure) |
| 25. | (structure) |
| 26. | (structure) |
| 27. | (structure) |

| Compound No | Structure |
|---|---|
| 28. | (structure) |
| 29. | (structure) |
| 30. | (structure) |
| 31. | (structure) |
| 32. | (structure) |
| 33. | (structure) |
| 34. | (structure) |

| Compound No | Structure |
|---|---|
| 35. | (structure) |
| 36. | (structure) |
| 37. | (structure) |
| 38. | (structure) |
| 39. | (structure) |
| 40. | (structure) |
| 41. | (structure) |

| Compound No | Structure |
|---|---|
| 42. | (structure) |
| 43. | (structure) |
| 44. | (structure) |
| 45. | (structure) |
| 46. | (structure) |
| 47. | (structure) |
| 48. | (structure) |

| Compound No | Structure |
|---|---|
| 49. | (structure) |
| 50. | (structure) |
| 51. | (structure) |
| 52. | (structure) |
| 53. | (structure) |
| 54. | (structure) |
| 55. | (structure) |

| Compound No | Structure |
|---|---|
| 56. | (structure) |
| 57. | (structure) |
| 58. | (structure) |
| 59. | (structure) |
| 60. | (structure) |
| 61. | (structure) |
| 62. | (structure) |

| Compound No | Structure |
|---|---|
| 63. | 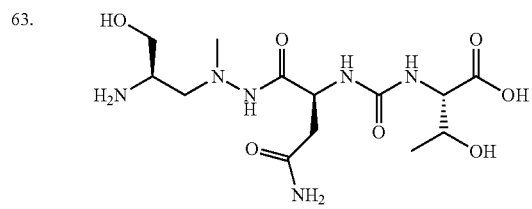 |
| 64. | 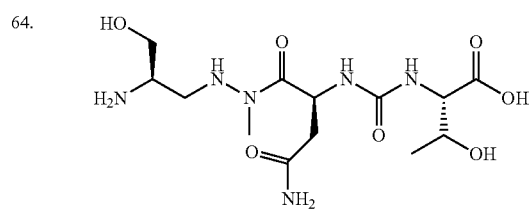 |
| 65. | 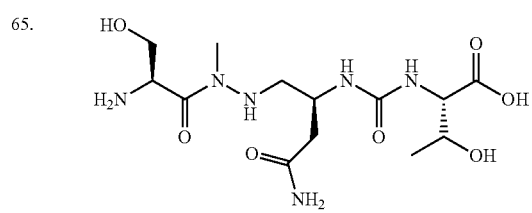 |
| 66. | 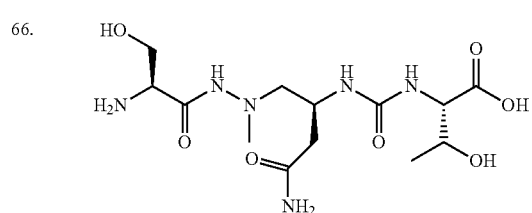 |
| 67. | 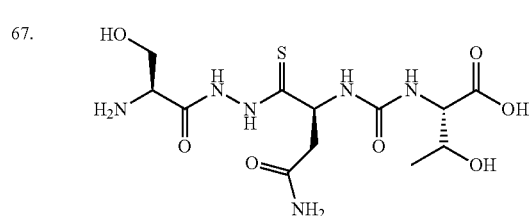 |
| 68. | 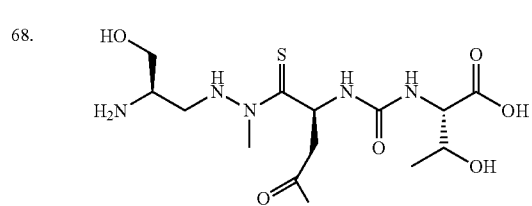 |
| 69. | 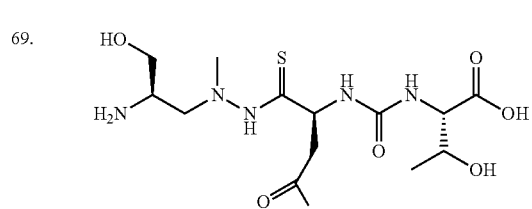 |
| Compound No | Structure |
|---|---|
| 70. | 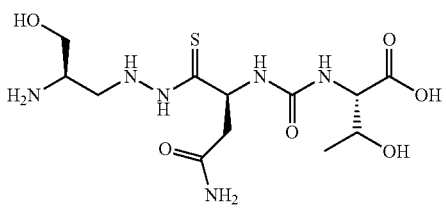 |
| 71. | 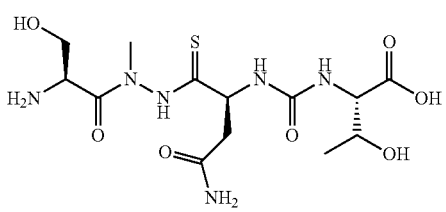 [SMILES: CC(O)[C@H](NC(=S)N[C@@H](CC(N)=O)C(=O)NN(C)C(=O)[C@@H](N)CO)C(=O)O] |
| 72. | 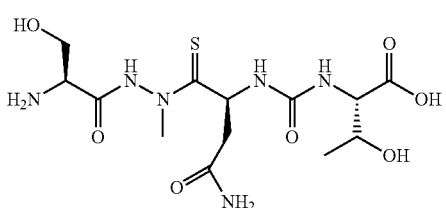 |
| 73. | 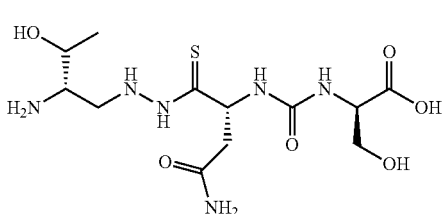 |
| 74. | 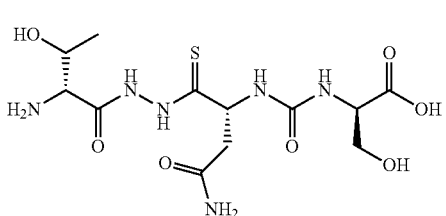 |
| 75. | 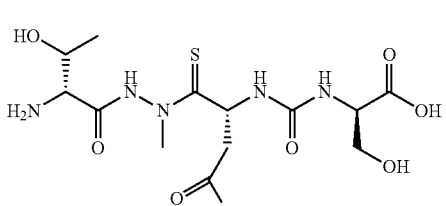 |
| 76. | 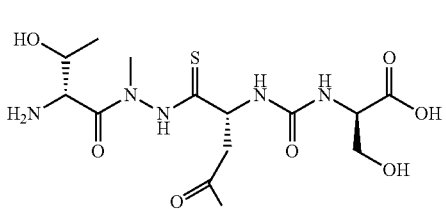 |

| Compound No | Structure |
|---|---|
| 77. | (structure) |
| 78. | (structure) |
| 79. | (structure) |
| 80. | (structure) |
| 81. | (structure) |
| 82. | (structure) |
| 83. | (structure) |
| 84. | (structure) |
| 85. | (structure) |
| 86. | (structure) |
| 87. | (structure) |
| 88. | (structure) |
| 89. | (structure) |
| 90. | (structure) |

| Compound No | Structure |
|---|---|
| 91. | (structure) |
| 92. | (structure) |
| 93. | (structure) |
| 94. | (structure) |
| 95. | (structure) |
| 96. | (structure) |
| 97. | (structure) |

| Compound No | Structure |
|---|---|
| 98. | (structure) |
| 99. | (structure) |
| 100. | (structure) |
| 101. | (structure) |
| 102. | (structure) |
| 103. | (structure) |
| 104. | (structure) |

| Compound No | Structure |
|---|---|
| 105. | (structure) |
| 106. | (structure) |
| 107. | (structure) |
| 108. | (structure) |
| 109. | (structure) |
| 110. | (structure) |
| 111. | (structure) |
| 112. | (structure) |
| 113. | (structure) |
| 114. | (structure) |
| 115. | (structure) or |
| 116. | (structure) | or a stereoisomer thereof or a pharmaceutically acceptable salt thereof.

10. A pharmaceutical composition comprising at least one compound according to claim 1 and/or a pharmaceutically acceptable salt or a stereoisomer thereof, and a pharmaceutically acceptable carrier or excipient.

11. The pharmaceutical composition of claim 10 further comprising at least one additional pharmaceutical agent wherein the said additional pharmaceutical agent is an anticancer agent, chemotherapy agent, or antiproliferative compound.

\* \* \* \* \*